United States Patent [19]
Edwards et al.

[11] Patent Number: 5,899,917
[45] Date of Patent: May 4, 1999

[54] METHOD FOR FORMING A STENT IN SITU

[75] Inventors: Stuart D. Edwards, Portola Valley; Thomas C. Wehman, Cupertino; Theodore L. Parker, Danville; Theodore Kucklick, Los Gatos; Peter Park, Santa Clara; Alan Stein, Moss Beach; Eugene V. Skalnyi, Mountain View, all of Calif.

[73] Assignee: CardioSynopsis, Inc., Sunnyvale, Calif.

[21] Appl. No.: 08/984,481

[22] Filed: Dec. 1, 1997

Related U.S. Application Data

[63] Continuation-in-part of application No. 08/857,323, May 16, 1997, which is a continuation-in-part of application No. 08/815,096, Mar. 12, 1997, which is a continuation-in-part of application No. 08/982,120, Dec. 1, 1997, which is a continuation-in-part of application No. 08/982,247, Dec. 1, 1997, which is a continuation-in-part of application No. 08/982,246, Dec. 1, 1997.

[51] Int. Cl.$^6$ ...................................................... A61F 2/06
[52] U.S. Cl. ............................................................. 606/195
[58] Field of Search ........................................ 606/151–158, 606/191, 192, 193, 194, 195–200; 623/1, 12, 11; 604/8, 104; 600/36

[56] References Cited

U.S. PATENT DOCUMENTS

| | | |
|---|---|---|
| 5,092,841 | 3/1992 | Spears . |
| 5,100,429 | 3/1992 | Sinofsky et al. . |
| 5,213,580 | 5/1993 | Slepian et al. . |
| 5,256,141 | 10/1993 | Gencheff et al. . |
| 5,328,471 | 7/1994 | Slepian . |
| 5,334,201 | 8/1994 | Cowan . |
| 5,344,444 | 9/1994 | Glastra . |
| 5,443,495 | 8/1995 | Buscemi et al. . |
| 5,464,419 | 11/1995 | Glastra . |
| 5,500,013 | 3/1996 | Buscemi et al. . |
| 5,529,653 | 6/1996 | Glastra . |
| 5,551,954 | 9/1996 | Buscemi et al. . |
| 5,554,182 | 9/1996 | Dinh et al. . |
| 5,571,166 | 11/1996 | Dinh et al. . |
| 5,575,815 | 11/1996 | Slepian et al. . |
| 5,599,307 | 2/1997 | Bacher et al. . |
| 5,612,050 | 3/1997 | Rowe et al. . |
| 5,634,946 | 6/1997 | Slepian . |
| 5,653,736 | 8/1997 | Glastra . |
| 5,662,609 | 9/1997 | Slepian . |
| 5,662,712 | 9/1997 | Pathak et al. . |
| 5,665,063 | 9/1997 | Parhak et al. . |
| 5,674,287 | 10/1997 | Slepian et al. . |
| 5,698,189 | 12/1997 | Rowe et al. . |

FOREIGN PATENT DOCUMENTS

| | | |
|---|---|---|
| WO 94/24962 | 11/1994 | WIPO . |
| WO 96/00102 | 1/1996 | WIPO . |
| WO 96/11021 | 4/1996 | WIPO . |
| WO 96/11671 | 4/1996 | WIPO . |
| WO 96/29080 | 9/1996 | WIPO . |
| WO 96/29370 | 9/1996 | WIPO . |
| WO 96/29987 | 10/1996 | WIPO . |
| WO 97/05185 | 2/1997 | WIPO . |
| WO 97/33628 | 9/1997 | WIPO . |

*Primary Examiner*—Michael Buiz
*Assistant Examiner*—Vikki Trinh
*Attorney, Agent, or Firm*—Wilson Sonsini Goodrich & Rosati

[57] ABSTRACT

A method is provided for forming a stent within a body lumen. According to the method, a distal catheter body is advanced within a body lumen to a section of a body lumen at which a stent is to be formed. One or more expandable members attached to the distal catheter body are expanded such that sections of the body lumen proximal and distal to the stent formation section of the body lumen are occluded, the distal catheter body in combination with the body lumen defining a mold space. A fluent pre-stent composition is delivered to the mold space from outside the body lumen which is continuously in fluent state during pre-stent composition delivery from outside the body lumen to the mold space. The fluent pre-stent composition is then transformed within the mold space to a non-fluent stent composition to form a stent within the mold space.

28 Claims, 25 Drawing Sheets

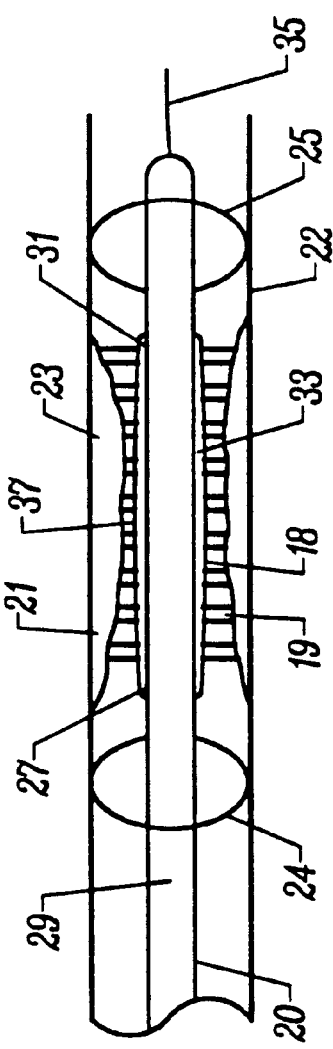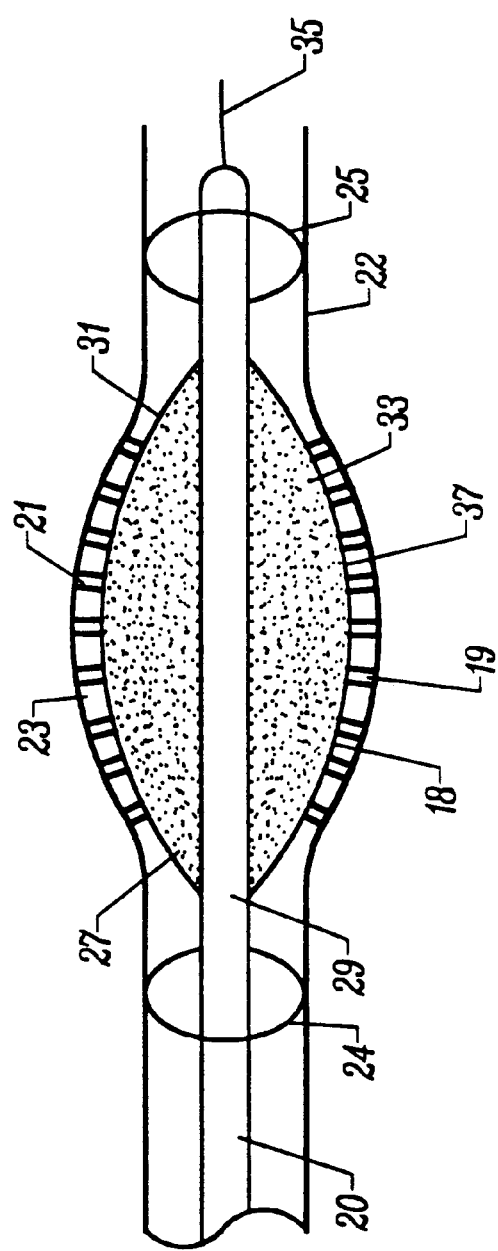

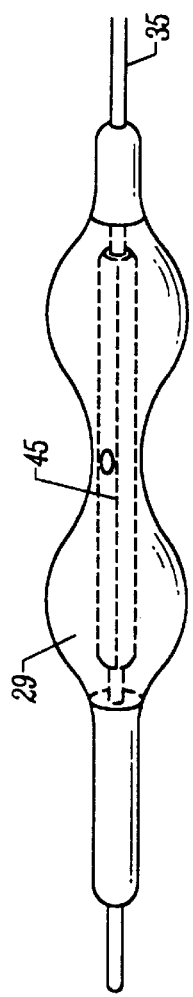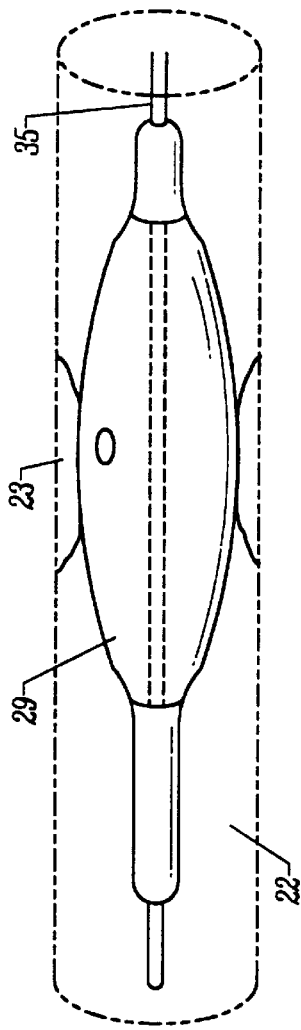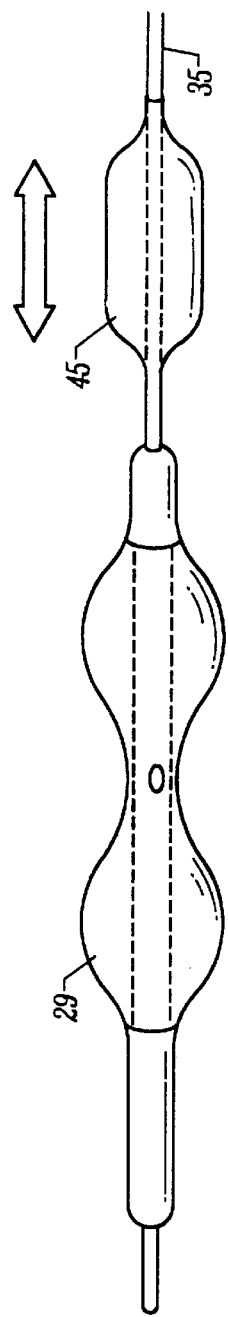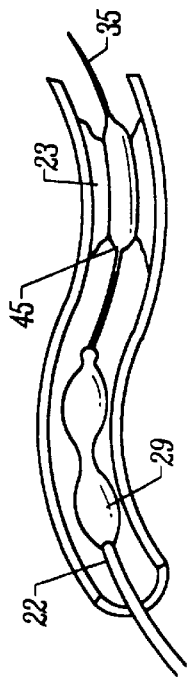
FIG. 3E
FIG. 3F
FIG. 3G
FIG. 3H

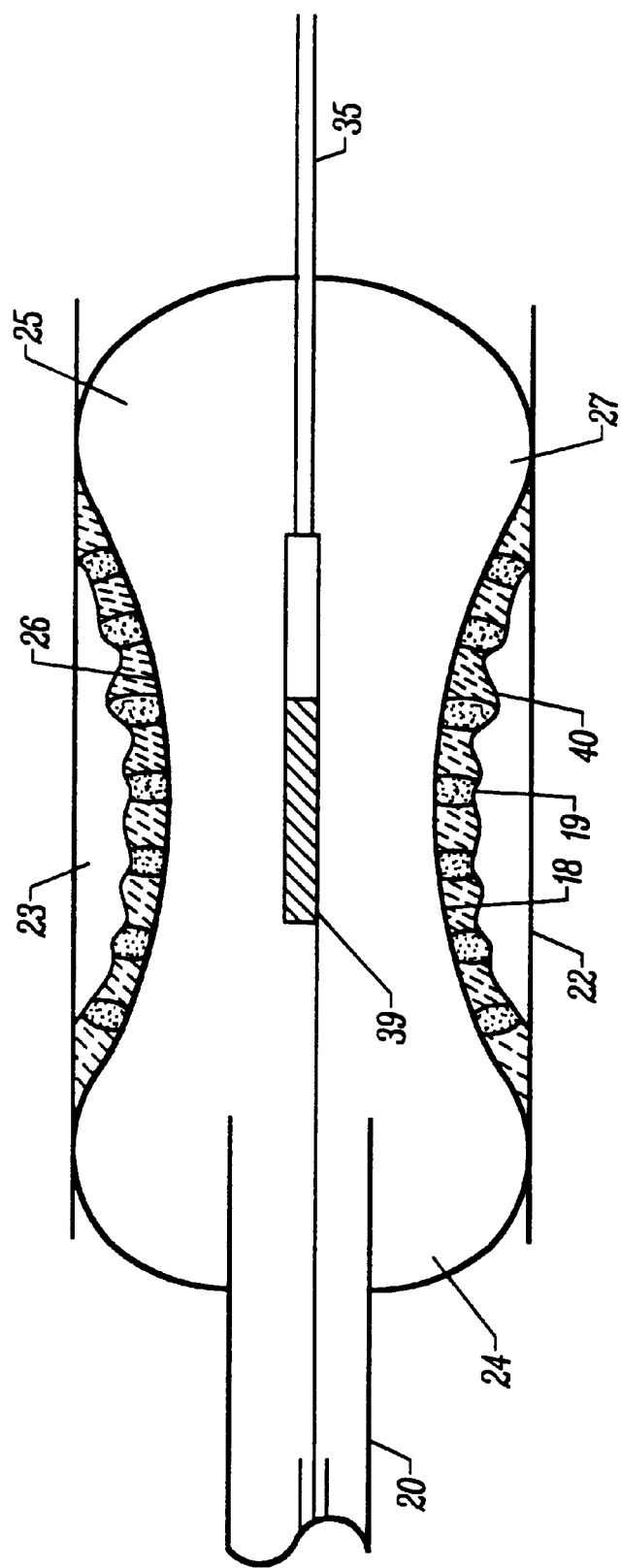

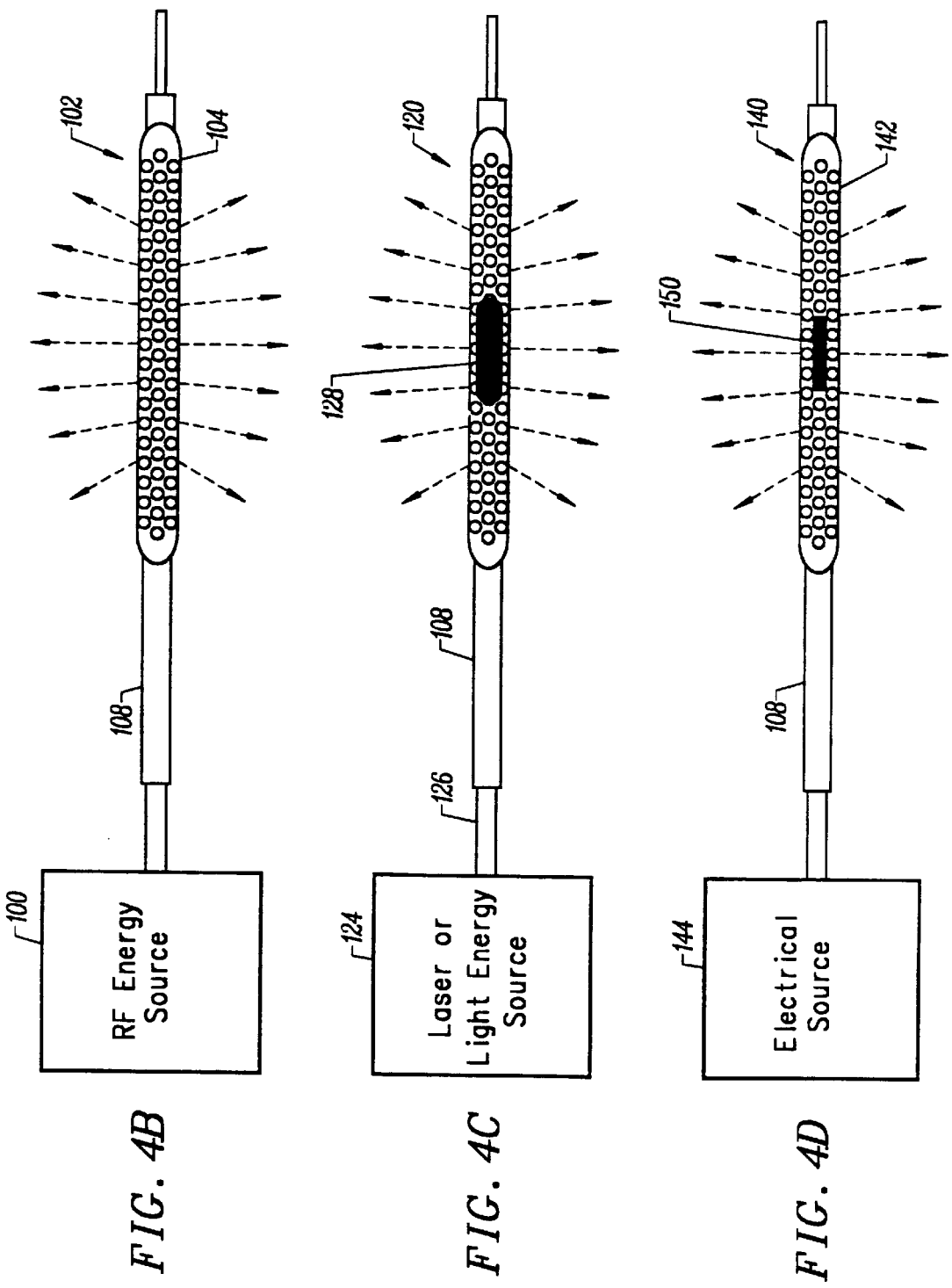

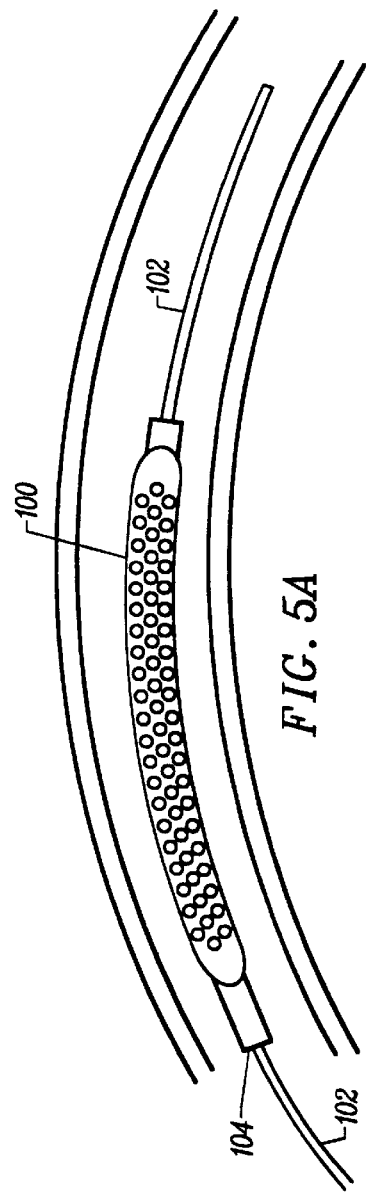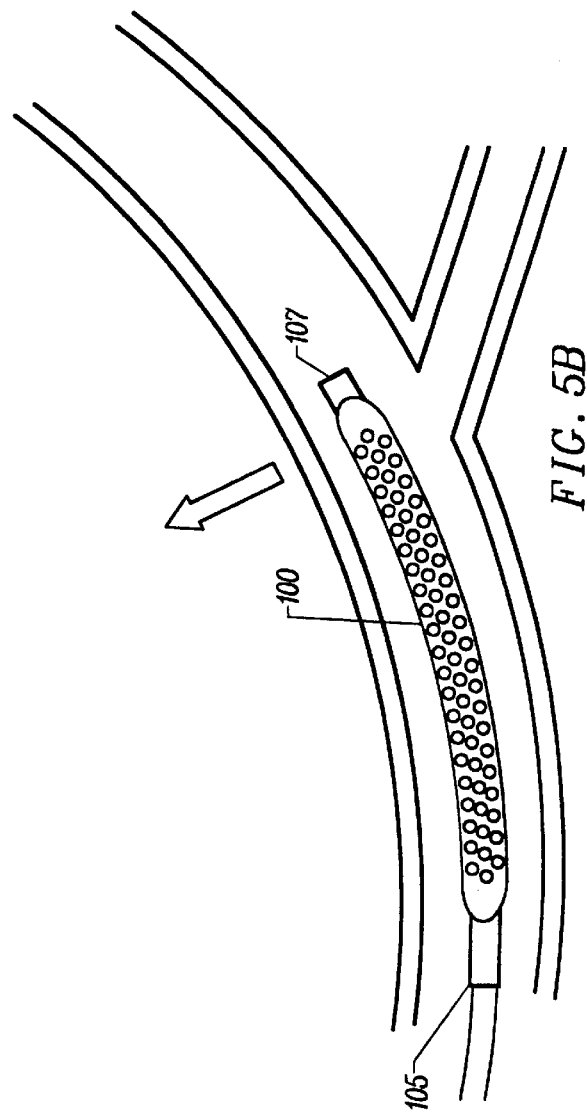

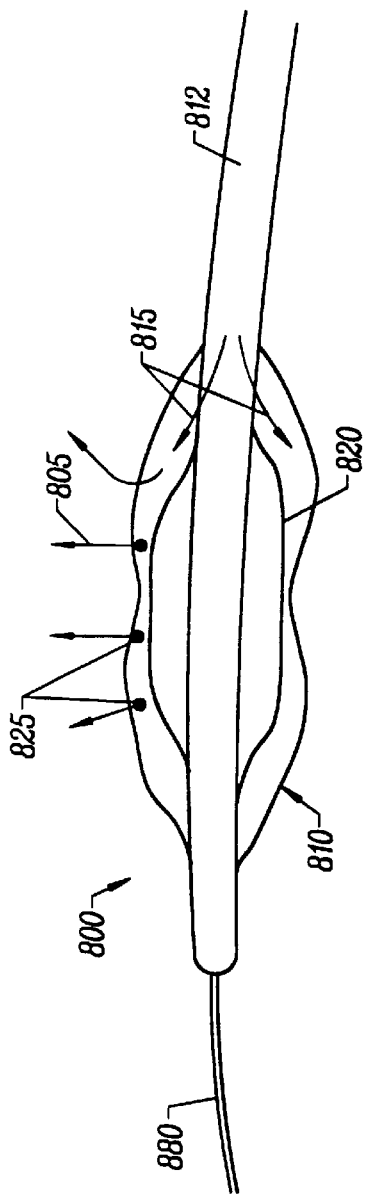
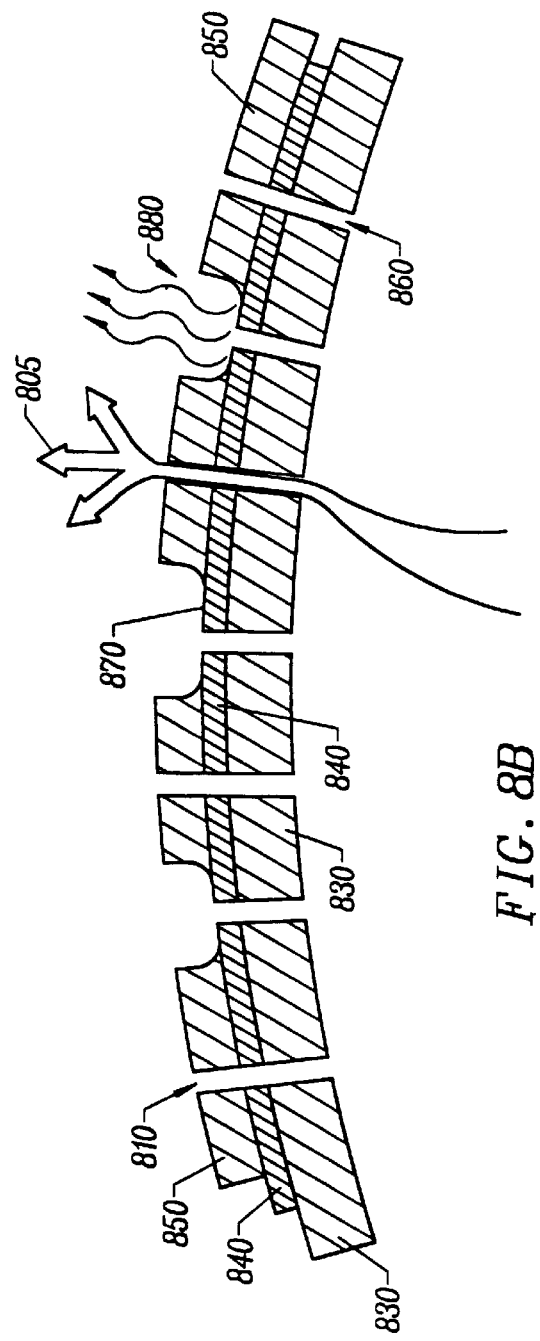
FIG. 8A
FIG. 8B

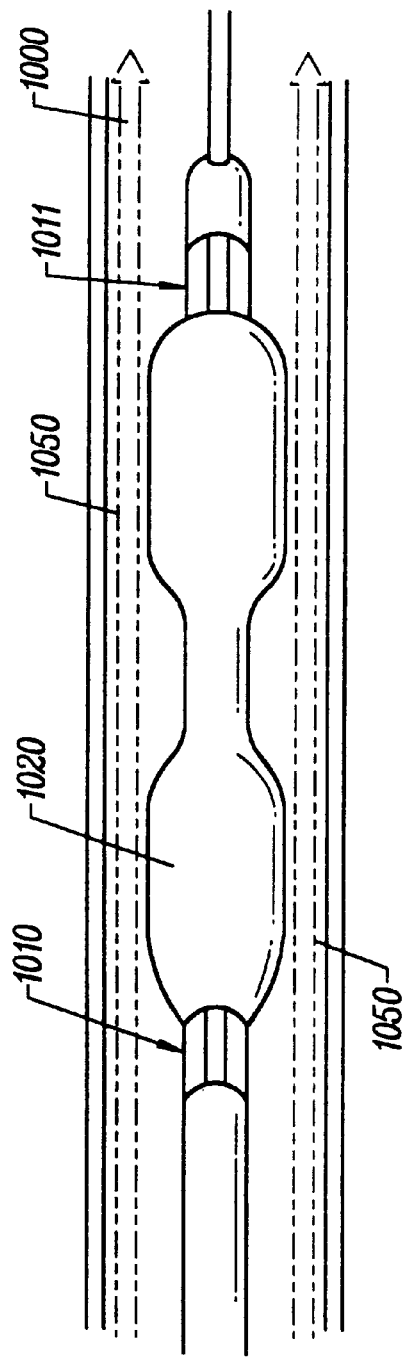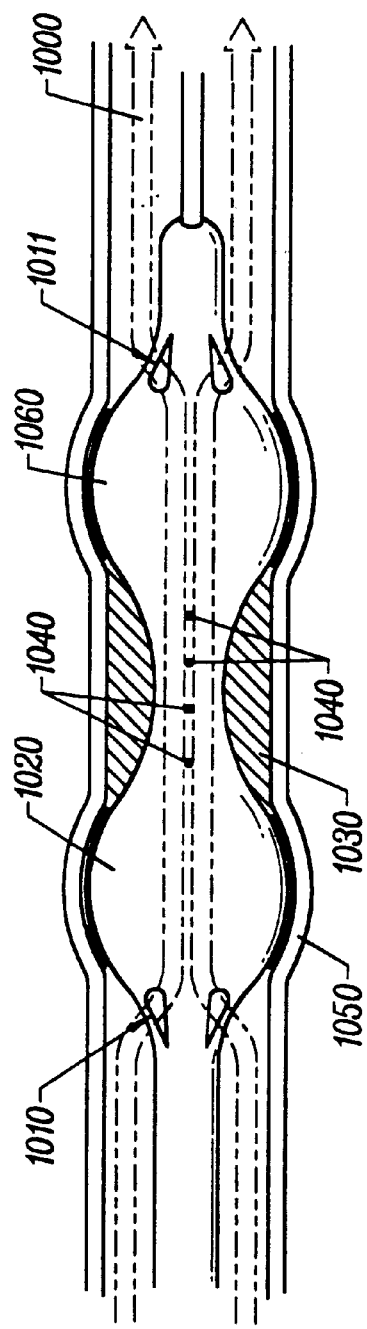
FIG. 10A
FIG. 10B

FIG. 13
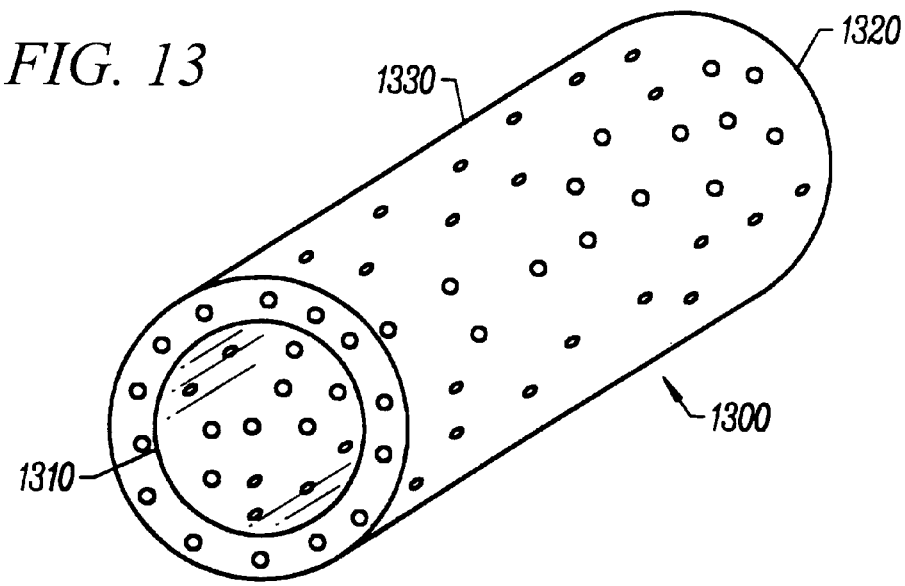
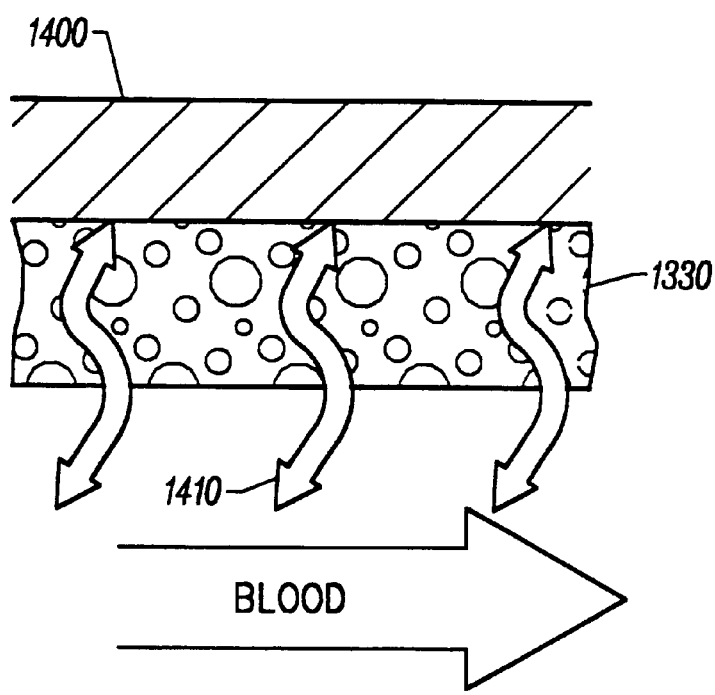
FIG. 14

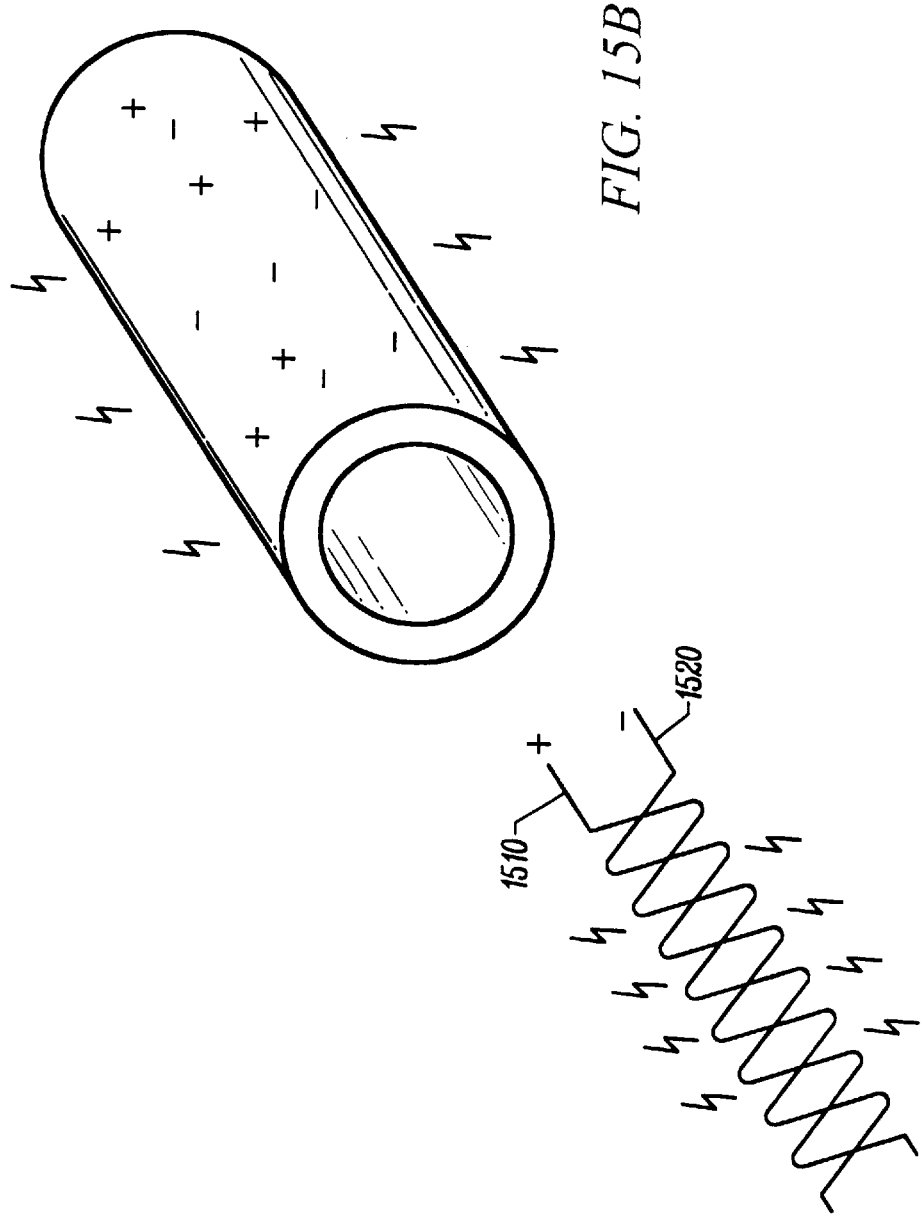

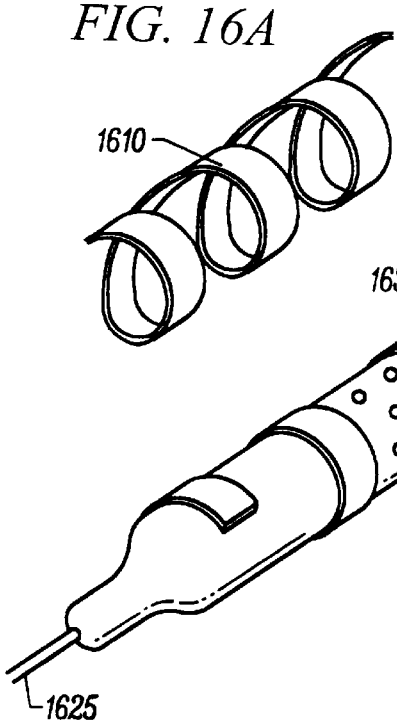
FIG. 16A
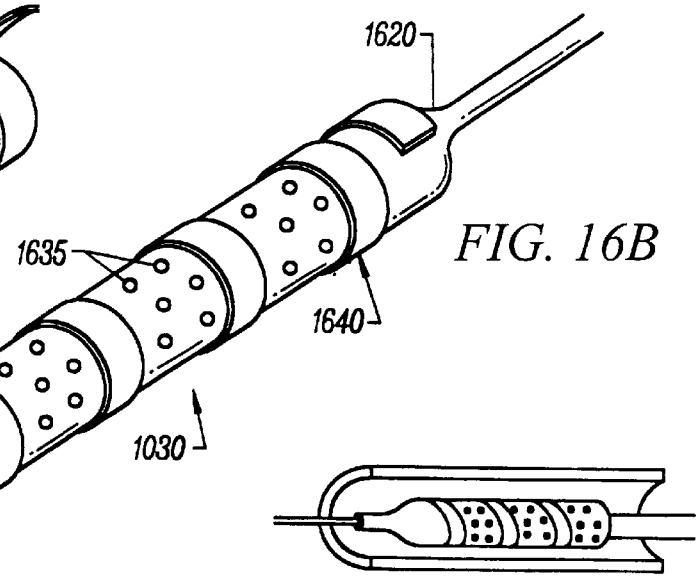
FIG. 16B
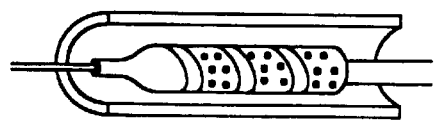
FIG. 16C
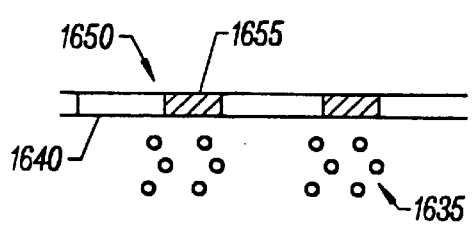
FIG. 16D
FIG. 16E
FIG. 16F
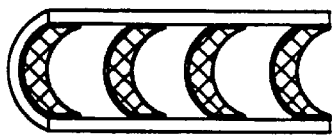
FIG. 16G

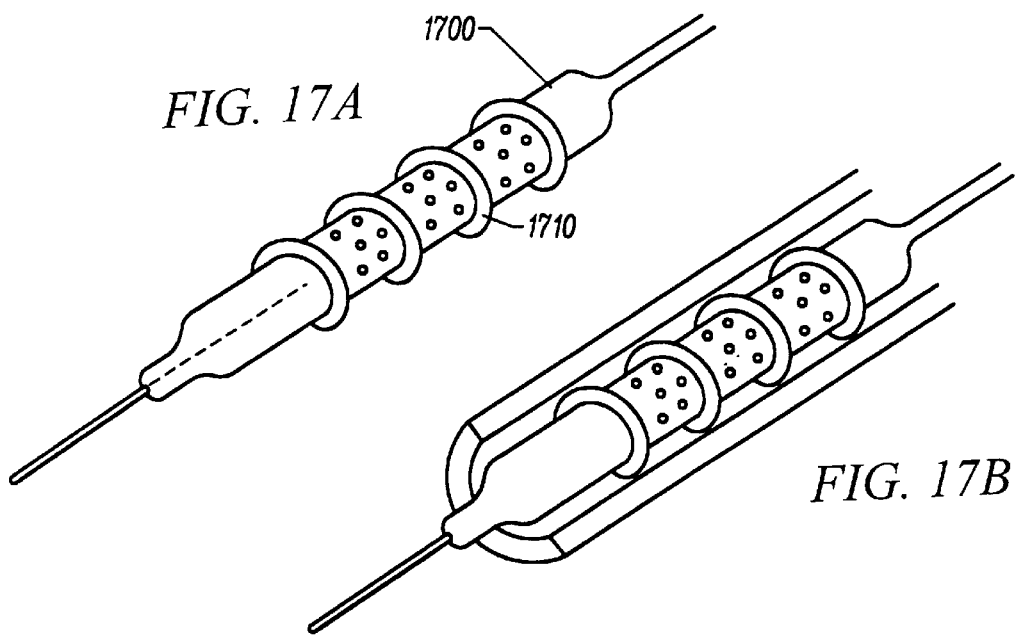
FIG. 17A
FIG. 17B
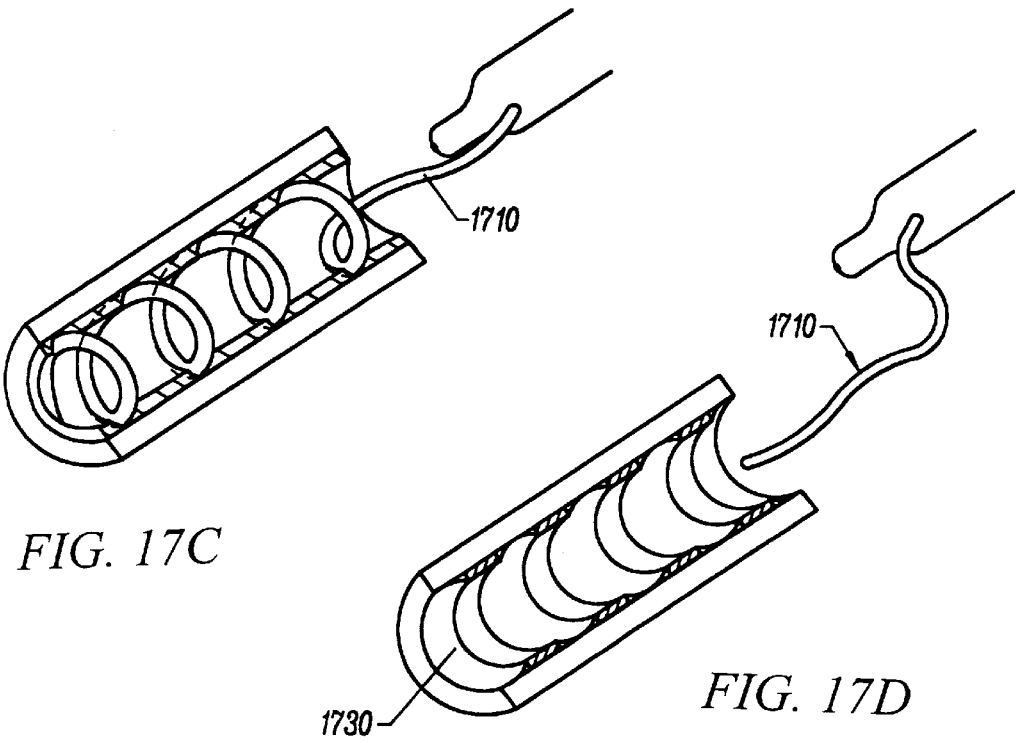
FIG. 17C
FIG. 17D

METHOD FOR FORMING A STENT IN SITU

This application is a continuation-in-part of U.S. patent application Ser. No. 08/857,323; filed: May 16, 1997, entitled "A Radiopaque Bioresorbable Stent, Created in Situ", which is a continuation-in-part U.S. patent application Ser. No. 08/815,096; filed: Mar. 12 ,1997, entitled "A Bioresorbable Stent, Created in Situ", which is a continuation-in-part of U.S. application Ser. No. 08/982,120; filed: Dec. 1, 1997, entitled "Device for Forming a Stent In Situ", which is a continuation-in-part of U.S. application Ser. No. 08/982,247; filed: Dec. 1, 1997, entitled "In Situ Formed Stent", which is a continuation-in-part of U.S. application Ser. No. 08/982,246; filed: Dec. 1, 1997, entitled "In Situ Formed Fenestrated Stent", all of which are incorporated by reference.

BACKGROUND OF THE INVENTION

1. Field Of The Invention

The present invention relates generally to stents for body lumens. More specifically, the present invention relates to stents created in situ within a body lumen through the conversion of a fluent material to a non-fluent material where the fluent material is delivered to the body lumen in a fluent state.

2. Discussion Of Related Art

Angioplasty is a procedure for treating blood vessels or arteries which have become narrowed by plaque deposits. Typically, a catheter comprising an inflatable balloon is advanced along a path of travel through the artery to a narrowed or stenosed region. The balloon is inflated at the stenosed region of the artery causing it to be expanded. The balloon is then deflated and withdrawn.

The effect of inflating a balloon against a narrowed arterial wall typically produces injuries. When an angioplasty balloon is inflated, the single layer of cells constituting the endothelial lining typically are torn away. Also, the inflation of the angioplasty balloon may induce fissures or other injuries to the arterial wall. The loss of endothelial cells and injury to the arterial wall create an irregular surface. Such tears and unconformities in the arterial wall, along with the loss of the endothelial layer, activate the coagulation system. This in turn may form sites for promoting the growth of blood clots, which then again occlude and narrow the artery.

Conventional cardiology procedures include the introduction of a stent to a target site in a blood vessel or artery after balloon angioplasty has been performed to provide structural support to the vessel.

Conventional stents typically are fabricated of metal or plastic and include a central lumen to permit the flow of blood through the blood vessel. The metal or plastic composition is necessary to provide sufficient rigidity to hold the blood vessel or artery open. Conventional stents are fabricated outside of the body and introduced into the blood vessel or artery on the outside of a catheter. The stent is then advanced along a path of travel to the point of intervention. As the stent is advanced through the blood vessel or artery, the inherent stiffness and pre-formed configuration of the stent often causes trauma to the vascular wall and the endothelial lining.

Devices have been developed for delivering a polymeric preformed stent on the outside of a catheter which is expanded and hardened within the vessel lumen. See U.S. Pat. Nos. 5,100,429, 5,334,201, 5,344,444, 5,443,495, 5,464,419, 5,529,653, 5,599,307, 5,634,946 and 5,653,736.

Several devices have also been developed for applying a fluent material to the surface of a vessel lumen. See U.S. Pat. Nos. 5,634,946, 5,612,050, 5,599,307, 5,575,815, 5,213,580, 5,328,471, 5,256,141, 5,092,841, and WO 96/00102. These devices and methods do not teach forming a stent from the fluent material.

Despite the numerous stents and stent delivery devices which have been developed to date, a need still exists for a stent which can be delivered and positioned with a minimum of trauma to vascular tissue which has already been damaged by angioplasty. There is also a need for a new type of stent which can be introduced to a target site in vascular lumen substantially without trauma and without contaminating the target site or any lesion with thrombogenic material which would cause restenosis. There is also a need for an improved stent which once placed in the vascular lumen can prevent restenosis and at the same time not create a permanent danger to the patient in the event the stent is dislodged. Also needed is a stent and a method for delivering the stent which can be considerably downsized over what is presently available and which can be delivered to a target site without injury to the delicate, single layer of cells constituting the endothelial lining.

SUMMARY OF INVENTION

It is a principle object of the invention to provide a device, a method, and a composition for forming shaped articles in a body lumen in situ wherein the article serves a mechanical function. It is also a principle object of the invention to provide the shaped articles formed in situ within the body lumen. In a preferred embodiment, the shaped articles include a lumen which allows biological material which would otherwise be flowing through the body lumen to flow through the shaped article.

Another object of the invention is to provide a device, a method, and a composition for forming a stent in a body lumen in situ from a fluent composition that is provided in a fluent state through the body lumen to the site of stent formation. According to this embodiment, the body lumen and stent forming device form a mold space within which the fluent composition is transformed into a nonfluent composition in the shape of a stent.

Another object of the invention is to provide a device, a method, and a composition for forming a fenestrated stent in situ in a body lumen from a fluent composition that is provided in a fluent state through the body lumen to the site of stent formation. According to this embodiment, the body lumen and stent forming device form a mold space within which the fluent composition is transformed into a nonfluent composition in the shape of a stent with a series of fenestrations.

Another object of the invention is to provide a device, a method, and a composition for forming a stent in situ in a body lumen from a fluent composition that is provided in a fluent state through the body lumen to the site of stent formation where energy is delivered at the site of stent formation to cause the fluent composition to become transformed into a nonfluent composition. In one embodiment, energy is delivered via a catheter. In another embodiment, energy is delivered via a guidewire. In a preferred embodiment, the energy is electromagnetic energy and more specifically either RF or microwave energy.

It is a further object of the invention to provide a device, a method, and a composition for forming stents in situ in the human vascular system, particularly coronary arteries.

It is a further object of the invention to provide a device, a method, and a composition for forming multi-layered stents in situ in the human vascular system, particularly coronary arteries.

It is a further object of the invention to provide a device, a method and a composition for reducing the rate of restenosis and/or rethrombosis in the human vascular system following interventional surgical procedures, particularly interventional cardiology procedures such as coronary balloon angioplasty.

It is a further object of the invention to provide a device, a method, and a composition for treating a diseased vascular lumen with longer and fewer stents than the vascular advancement path to the diseased area would otherwise allow with regard to ex vivo fabricated stents.

It is a further object of the invention to provide a device, a method, and a composition for treating a diseased vascular lumen with stents which are conformal to the intima surface of the lumen and exhibit greater adhesion thereto. This is achieved by delivering a fluent material to the stent formation site and allowing the fluent material to flow to conform to the surface of the lumen.

It is a further object of the invention to provide a device, a method, and a composition for delivering a therapeutic drug to a diseased vascular lumen with a stent according to the present invention.

It is a further object of the invention to provide a device, a method, and a composition for forming a stent in situ according to the present invention which has a desired porosity.

It is a further object of the invention to provide a device, a method, and a composition for providing a scaffolding for delivery of cells to a diseased coronary artery, particularly cells capable of releasing VEGF (vascular endothelial growth factor) to a diseased coronary artery via a stent and more preferably a fenestrated stent.

It is a further object of the invention to deliver a therapeutic substance capable of enhancing the rate of endotheliazation of the intima to a diseased coronary artery via a stent and more preferably a fenestrated stent.

It is a further object of the invention to provide a multilayered stent where one layer is used to deliver therapeutic agents to and another layer is used for the mechanical support of a body lumen, such as a diseased coronary artery.

It is a further object of the invention to provide a balloon catheter that may be inflated inside a vascular structure to provide a mold cavity defined by the surface of the balloon and an intimal wall of the vascular structure.

It is a further object of the invention to provide a balloon catheter whose surface has been formed into a shape that is the compliment of the fenestrated stent shape provided by the in situ forming method.

It is a further object of the invention to provide a device with (i) a catheter with a multiplicity of lumens for conducting a fluent pre-stent material, a balloon inflation fluid, and energy from outside the body to the vascular area to be treated, and (ii) a compliant balloon attached to the catheter which allows egress of the fluid pre-stent material into a mold cavity.

These, and other, aspects of the present invention will be better appreciated and understood when considered in conjunction with the following description and the accompanying drawings. It should be understood, however, that the following description, while indicating preferred embodiments of the present invention and numerous specific details thereof, is given by way of illustration and not limitation. Many changes and modifications may be made within the scope of the present invention without departing from the spirit thereof, and the invention includes all such modifications.

BRIEF DESCRIPTION OF THE DRAWINGS

FIG. 4A illustrates a cross section view of a device for making a fenestrated stent, representing an embodiment of the invention.

FIG. 4B illustrates a schematic view of a first system for applying energy to a fluent pre-stent material to effect a change of state from a fluent state to a nonfluent state, representing an embodiment of the invention.

FIG. 4C illustrates a schematic view of a second system for applying energy to a fluent pre-stent material, representing an embodiment of the invention.

FIG. 4D illustrates a schematic view of a third system for applying energy to a fluent pre-stent material, representing an embodiment of the invention.

FIG. 5A illustrates a cross-sectional view of a first system for advancing and steering a catheter along a path of travel in a vascular lumen, representing an embodiment of the invention.

FIG. 5B illustrates a cross-sectional view of a second system for advancing and steering a catheter along a path of travel in a vascular lumen, representing an embodiment of the invention.

FIG. 8A illustrates a side view of a catheter for forming a stent, representing an embodiment of the invention.

FIG. 8B illustrates an expanded sectional view of a portion of the device shown in FIG. 8A.

FIG. 10A illustrates a cross-sectional view of a perfusion valve catheter system for forming a stent in a collapsed state with the perfusion valves closed, representing an embodiment of the invention.

FIG. 10B illustrates the system of FIG. 10A in an expanded state with the perfusion valves open.

FIG. 13 illustrates a perspective schematic view of a porous stent, representing an embodiment of the present invention.

FIG. 14 illustrates a schematic sectional view of the wall of a porous stent adjacent a vascular wall, representing an embodiment of the present invention.

FIGS. 15A–15B illustrate perspective views of stents, including electrodes.

FIGS. 16A–16G illustrate schematic views of a method, device and composition for forming a stent, representing an embodiment of the invention.

FIGS. 17A–17D illustrate schematic perspective views of a device, method, and composition for forming a stent, representing an embodiment of the invention.

DETAILED DESCRIPTION OF PREFERRED EMBODIMENTS

Figure 1A:
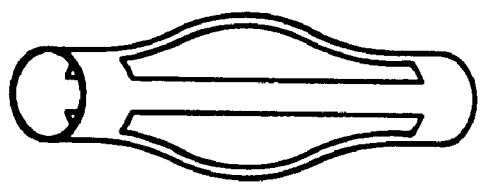
FIGS. 1A–1D illustrate isometric views of four different fenestrated stents, representing embodiments of the invention.
Figure 1B:
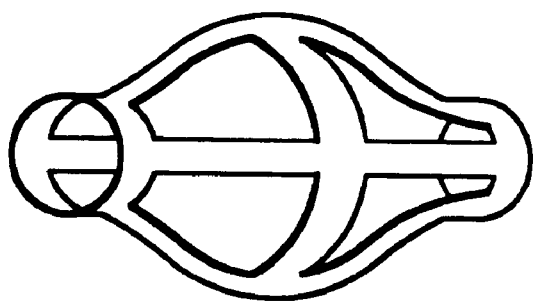
Figure 1C:
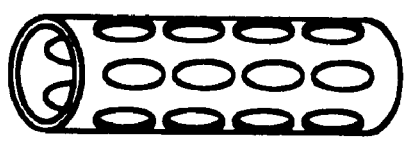
Figure 1D:
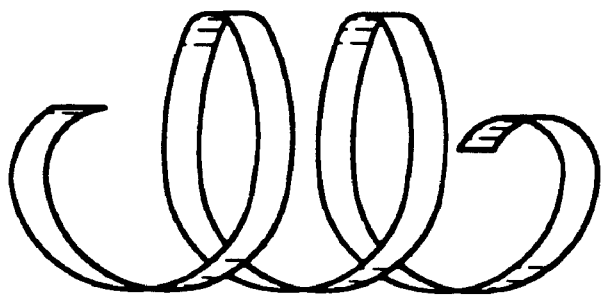
Figure 2A:
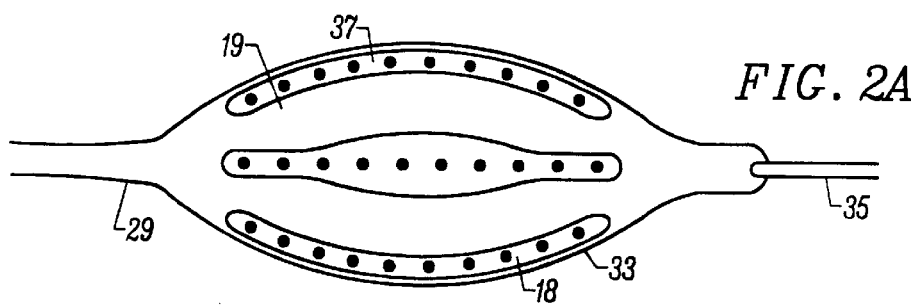
FIGS. 2A–2H illustrate isometric views of four different devices (FIGS. 2A, 2C, 2E, 2G) for making fenestrated stents in situ and the four corresponding stents (FIGS. 2B, 2D, 2F, 2H) made from the four depicted devices, representing embodiments of the invention.
Figure 2B:
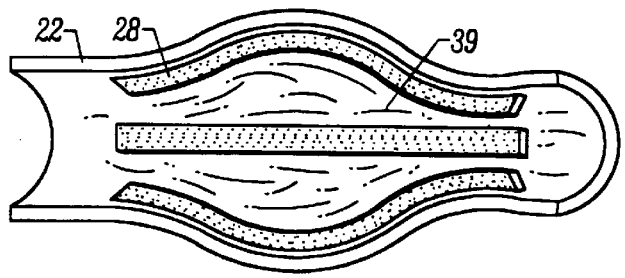
Figure 2C:
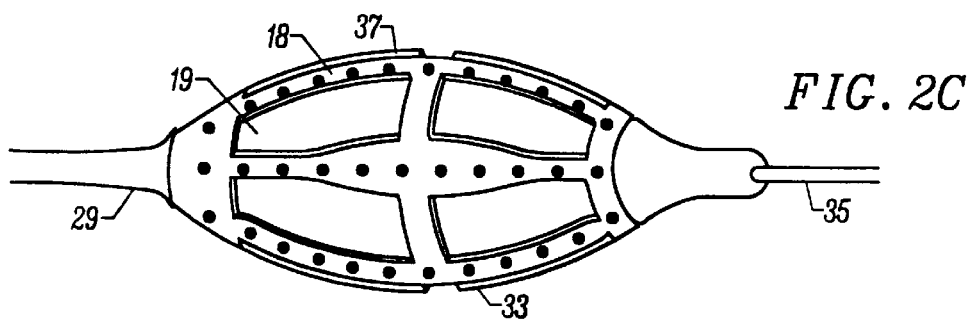
Figure 2D:
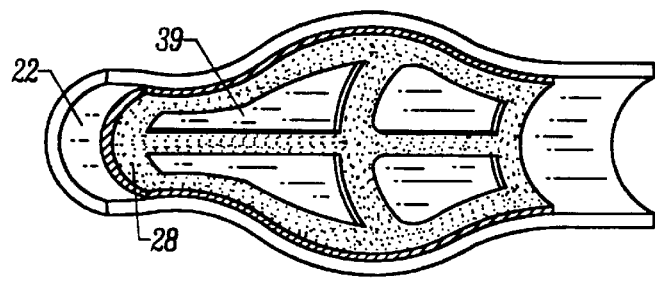
Figure 2E:
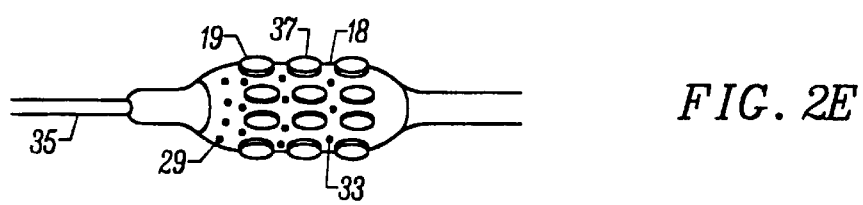
Figure 2F:
Figure 2G:
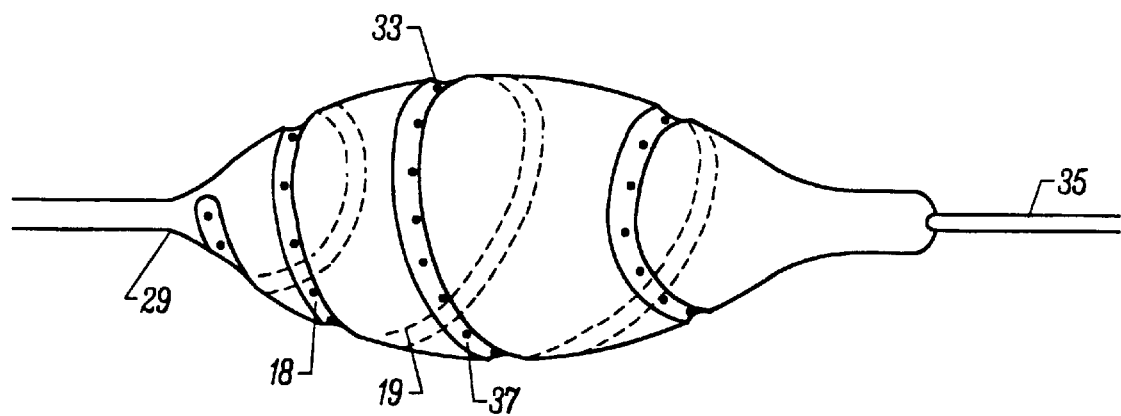
Figure 2H:
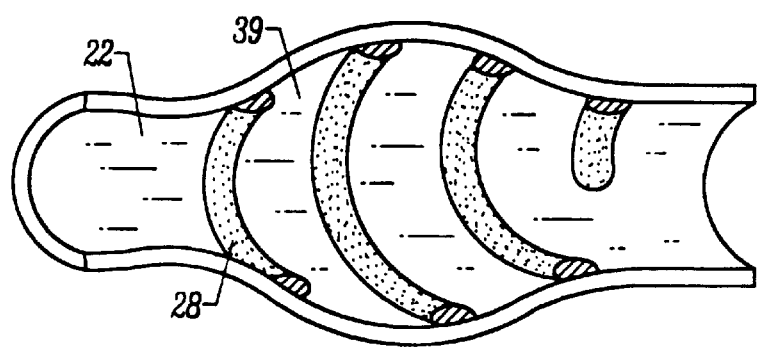

The present invention relates to a stent formed in a body lumen. In one embodiment, the stent includes an article shaped to provide support to a section of a body lumen and allow biological material which would otherwise flow through the body lumen to flow through the article, the article including a non-fluent stent composition in intimate contact with the section of the body lumen which was delivered through the body lumen to the section as a fluent pre-stent composition and transformed adjacent the section of the body lumen to the non-fluent stent composition.

In another embodiment of the invention, the stent includes an article shaped to provide support to a section of a body lumen and allow biological material which would otherwise flow through the body lumen to flow through the article, the article being formed by delivering a fluent pre-stent composition and an energy susceptible composition to a mold space defined by a section of a body lumen and a fluent pre-stent composition delivery device, and transforming the fluent pre-stent composition to a non-fluent stent composition within the mold space by introducing a form of energy which is preferentially absorbed by the energy susceptible composition.

In yet another embodiment of the invention, the stent includesan article shaped to provide support to a section of a body lumen and allow biological material which would otherwise flow through the body lumen to flow through the article, the article being formed by transforming a fluent pre-stent composition to a non-fluent stent composition using an energy susceptible composition and a form of energy which is preferentially absorbed by the energy susceptible composition.

The present invention also relates to a fenestrated stent formed in a body lumen. In one embodiment, the fenestrated stent includes an article shaped to provide support to a section of a body lumen and allow biological material which would otherwise flow through the body lumen to flow through the article, the article being formed with fenestrations by delivering a fluent pre-stent composition to a mold space defined by a section of a body lumen and a fluent pre-stent composition delivery device having members which define the fenestrations, and transforming the fluent pre-stent composition to a non-fluent stent composition within the mold space.

In yet another embodiment of the invention, the fenestrated stent includes an article shaped to provide support to a section of a body lumen, allow biological material which would otherwise flow through the body lumen to flow through the article, and include fenestrations, the fenestrated article including a non-fluent stent composition in intimate contact with the section of the body lumen which was delivered through the body lumen to the section as a fluent pre-stent composition and transformed adjacent the section to the non-fluent stent composition.

In yet another embodiment of the invention, the stent includes an article shaped to provide support to a section of a body lumen and allow biological material which would otherwise flow through the body lumen to flow through the article, the article including a non-fluent stent composition in intimate contact with the section of the body lumen which was delivered through the body lumen to the section as a fluent pre-stent composition and transformed adjacent the section to the non-fluent stent composition; and a bioresorbable composition dispersed among the article which when bioresorbed leave fenestrations in the article.

With regard to any of the above embodiments for a stent or fenestrated stent, the stent may have one or more of the following features:

the stent defines a stent lumen having first and second ends, each end having a diameter, a section of the stent lumen positioned between the first and second ends having a diameter which is larger than the diameters of the lumen at the first and second ends;

the non-fluent stent composition includes an energy susceptible composition;

the non-fluent stent composition includes a microwave energy susceptible composition;

the non-fluent stent composition includes a material for dilating a mammalian vascular structure, preferably magnesium sulfate;

the article is shaped to interpenetrate fissures at the section of the body lumen;

the non-fluent stent composition includes linkages selected from the group consisting of carbonate, amide, peptide, and urethanes, ester, urea, ether, amino, thio, hydrocarbonyl, sulfonyl, sulfoxy, phosphate, and phosphite;

the non-fluent stent composition includes a radio opaque material;

the non-fluent stent composition has electrolytic properties;

the fluent pre-stent composition is transformed to the nonfluent stent composition using electromagnetic energy;

the fluent pre-stent composition is transformed to the nonfluent stent composition using radio frequency energy;

the fluent pre-stent composition is transformed to the nonfluent stent composition using microwave energy;

the non-fluent stent composition has pores for allowing the diffusion of biological material therethrough;

the non-fluent stent composition is bioresorbable;

the non-fluent stent composition includes a diffusible therapeutic agent;

the stent conforms to an interior surface of a blood vessel;

the stent conforms to an interior surface of a blood vessel which has undergone balloon angioplasty;

the stent conforms to an interior surface of a stenotic blood vessel containing plaque; and the non-fluent stent composition is interdispersed with the plaque.

The present invention also relates to a composition for forming a stent in a body lumen. In one embodiment, the composition includes a first fluent composition which can be transformed into a second nonfluent composition upon the application of thermal energy; and an energy susceptible composition admixed with the first fluent composition which preferentially absorbs microwave energy and catalyzes the transformation of the first fluent composition to the second non-fluent composition upon the application of microwave energy.

The present invention also relates to a catheter for forming a stent in a body lumen. In one embodiment, the catheter includes a distal catheter body having one or more fluent pre-stent composition delivery ports;

one or more expandable members attached to the distal catheter body for occluding proximal and distal sections of a body lumen so as to define a mold space therebetween and for radially expanding the body lumen within the mold space; and a lumen for delivering a fluent pre-stent composition from outside the body lumen to the expanded mold space through the one or more delivery ports.

In another embodiment, the catheter includes a distal catheter body having one or more fluent pre-stent composition delivery ports;

one or more expandable members attached to the distal catheter body for occluding proximal and distal sections of a body lumen so as to define a mold space therebetween;

one or more members extending from the distal catheter body to define a fenestration pattern in the mold space;

a lumen for delivering a fluent pre-stent composition from outside the body lumen to the expanded mold space through the one or more delivery ports; and an energy delivery mechanism for delivering energy into the expanded mold space to accelerate a transformation of the fluent pre-stent composition to a non-fluent stent composition.

In yet another embodiment, the catheter is for forming fenestrated stents and includes a distal catheter body having one or more fluent pre-stent composition delivery ports;

one or more expandable members attached to the distal catheter body for occluding proximal and distal sections of a body lumen so as to define a mold space therebetween;

one or more members extending from the distal catheter body to define a fenestration pattern in the mold space which detach from the distal catheter body after stent formation;

a lumen for delivering a fluent pre-stent composition from outside the body lumen to the expanded mold space through the one or more delivery ports; and an energy delivery mechanism for delivering energy into the expanded mold space to accelerate a transformation of the fluent pre-stent composition to a non-fluent stent composition.

With regard to any of the above embodiments for a stent or fenestrated stent forming catheter, the catheter may have one or more of the following features:

the one or more expandable members create a mold space which is narrower at the proximal and distal sections of the body lumen than between the proximal and distal sections;

the catheter further includes an energy delivery mechanism for delivering energy into the expanded mold space to accelerate a transformation of the fluent pre-stent composition to a non-fluent stent composition;

the catheter further includes an energy delivery mechanism which is attached to the distal catheter body;

the catheter further includes an energy delivery mechanism which is attached to a guide wire;

the catheter further includes an energy delivery mechanism which delivers RF energy;

the catheter further includes an energy delivery mechanism which delivers microwave energy;

the catheter includes a steerable tip distal to the distal catheter body;

the catheter further includes an expandable member for performing balloon angioplasty;

the catheter further includes an expandable member for performing balloon angioplasty which is distal to the distal catheter body;

the catheter further includes an expandable member for performing balloon angioplasty which is proximal to the distal catheter body;

the catheter further includes an expandable member for performing balloon angioplasty which is attached to the distal catheter body;

the catheter further includes an expandable member for performing balloon angioplasty which is positioned within the one or more expandable members for defining a mold space;

the distal catheter body includes a perfusion lumen for allowing biological material to flow through the body lumen when the lumen is occluded by the one or more expandable members;

the distal catheter body includes a perfusion lumen for allowing biological material to flow through the body lumen when the one or more expandable members are expanded;

the distal catheter body is sized to be passed within a blood vessel;

the distal catheter body is sized to be passed within a blood vessel which has undergone balloon angioplasty;

the distal catheter body is sized to be passed within a stenotic blood vessel;

the one or more expandable members also radially expand the body lumen within the mold space; and the distal catheter body includes fenestration pattern forming members which define a fenestration pattern selected from the group consisting of one or more slits, holes, spirals, helixes, and double helixes.

The present invention also relates to methods for forming a stent within a body lumen. In one embodiment, the method includes advancing a distal catheter body within a body lumen to a section of the body lumen at which a stent is to be formed; expanding one or more expandable members attached to the distal catheter body such that sections of the body lumen proximal and distal to the stent formation section of the body lumen are occluded, the distal catheter body in combination with the body lumen defining a mold space; delivering a fluent pre-stent composition within the mold space from outside the body lumen such that the pre-stent composition is continuously in fluent state during pre-stent composition delivery from outside the body lumen to the mold space; and transforming the fluent pre-stent composition to a nonfluent stent composition to form a stent within the mold space.

In another embodiment, the method includes advancing a distal catheter body within a body lumen to a section of the body lumen at which a stent is to be formed; expanding one or more expandable members attached to the distal catheter body such that sections of the body lumen proximal and distal to the stent formation section of the body lumen are occluded, the distal catheter body in combination with the body lumen defining a mold space; delivering a fluent pre-stent composition within the mold space from outside the body lumen such that the pre-stent composition is continuously in fluent state during pre-stent composition delivery from outside the body lumen to the mold space; and delivering microwave energy within the mold space to accelerate the transformation transforming the fluent pre-stent composition to a non-fluent stent composition to form a stent within the mold space.

In yet another embodiment, the method includes advancing a distal catheter body within a body lumen to a section of the body lumen at which a stent is to be formed; expanding one or more expandable members attached to the distal catheter body such that sections of the body lumen proximal and distal to the stent formation section of the body lumen are occluded, the distal catheter body in combination with the body lumen defining a mold space, the distal catheter body including one or more members extending from the distal catheter body which define a fenestration pattern within the mold space; delivering a fluent pre-stent composition within the mold space from outside the body lumen such that the pre-stent composition is continuously in fluent state during pre-stent composition delivery from outside the body lumen to the mold space; and transforming the fluent pre-stent composition to a nonfluent stent composition to form a fenestrated stent within the mold space.

In yet another embodiment, the method includes advancing a distal catheter body within a body lumen to a section of the body lumen at which a stent is to be formed; expanding one or more expandable members attached to the distal catheter body such that sections of the body lumen proximal and distal to the stent formation section of the body lumen are occluded, the distal catheter body in combination with the body lumen defining a mold space, the distal catheter body including one or more detachable members extending from the distal catheter body which define a fenestration pattern within the mold space; delivering a fluent pre-stent composition within the mold space from outside the body lumen such that the pre-stent composition is continuously in fluent state during pre-stent composition delivery from outside the body lumen to the mold space; transforming the fluent pre-stent composition to a non-fluent stent composition to form a fenestrated stent within the mold space; and detaching the one or more fenestration pattern defining members from the distal catheter body.

According to any one of the above methods, the method can optionally one or more of the following addition steps:
radially expanding the stent formation section of the body lumen prior to the transforming step;
performing balloon angioplasty prior to expanding the one or more expandable members;
delivering energy within the mold space to accelerate the transformation;
providing bypass during occlusion of the body lumen; and
providing bypass by opening a bypass lumen in the distal catheter body by expanding the one or more expandable members.

According to the method where the distal catheter body includes one or more detachable fenestration pattern defining members, the members can be bioresorbable and the method can further include the step of bioresorbing the one or more members to leave fenestrations in the stent. Bioresorption of the bioresorbable composition can also leave pores in the stent for the diffusion of biological material therethrough. The method can also include the step of moving the distal catheter body from the section of the body lumen at which the stent was formed, the one or more fenestration pattern defining members being detached in the process of moving the distal catheter body. The one or more detachable fenestration pattern defining members can also be separated from the fenestrated stent in the process of moving the distal catheter body.

The present invention and the various features and advantageous details thereof will now be explained more fully with reference to the nonlimiting embodiments that are illustrated in the accompanying drawings and detailed in the following description. Descriptions of well known components and processing techniques are omitted so as not to unnecessarily obscure the present invention in detail.

1. System Overview

The present invention relates to devices, methods, and compositions for forming shaped articles in a body lumen in situ for example, a human body lumen (vas), such as a narrowed or stenosed artery or vein. In a preferred embodiment, the shaped articles include a lumen which allows biological material which would otherwise be flowing through the body lumen to flow through the shaped article.

According to the present invention, the shaped article is formed in a body lumen in situ from a fluent composition that is provided in a fluent state through the body lumen to the site of the shaped article's formation. According to the present invention, the body lumen forms a portion of a mold space within the body lumen within which the fluent composition is transformed into a nonfluent composition in the shape of the shaped article.

A device according to the present invention relates to a catheter for minimally invasively forming the shaped article in the body lumen. A method according to the present invention relates to positioning the catheter in the body lumen and then delivering a fluent composition via the catheter through the body lumen to the site of the shaped article's formation. The catheter in combination with the body lumen form a mold space within the body lumen within which the fluent composition is transformed, preferably with the addition of energy, into a nonfluent composition in the shape of the shaped articule.

In one embodiment, the shaped article is a stent which is formed by expanding at least one balloon, deploying a fluent pre-stent composition from within the catheter to the site where the stent is to be formed, transforming the fluent pre-stent composition into a non-fluent stent composition, and deflating the at least one balloon. In a preferred embodiment, energy or a chemical catalyst is introduced to cause the transformation of the fluent pre-stent composition to a non-fluent stent composition. In instances where the application refers to forming a stent, it should be understood that such teaching should also be interpreted as applying to the formation of other shaped articles.

The present invention can also be used to form fenestrated stents. As used herein, the term "fenestrated stent" refers to a generally tubularly shaped article for lining the inner lumenal surface of a body lumen which includes one or more holes (fenestrations) along the wall of the tubular article. The fenestrations of such stents can have any shape including, but not limited to, geometric shapes such as polygons (e.g., squares, rectangles, and diamonds), curved shapes such as circles and ellipses, and irregular shapes. The fenestrations may also result in the stent taking the form of a spiral, helix, double helix, or spiral, with, or without, circular end caps. In general, any fenestrated stent which may be formed in situ using a catheter according to the present invention is intended to fall within the scope of the present invention.

2. Apparatus

FIGS. 1A–1D illustrate a series of different fenestrated stent designs. These stent designs are complimentary to the shape of the devices that form them. The stent designs illustrated in FIGS. 1A–1D are intended to be illustrative of the numerous different fenestrated stent designs which are possible according to the invention and are not intended to be limiting.

According to the present invention, a fenestrated stent is formed within a body lumen by the in situ conversion of a fluent pre-stent composition to a non-fluent stent composition. The shape of the fenestrated stent is defined by the inter-relationship between a distal catheter body on a catheter according to the present invention and the body lumen in which the catheter is positioned, the body lumen and distal catheter body defining a mold space for forming the stent. The fluent pre-stent composition is provided within the mold space and then converted into a non-fluent stent composition. By designing the catheter to have particular shaped and positioned members extending from its surface, a fenestrated stent having a particular design may be formed. For example, the fenestrated stents may be in the form of a cylinder with one or more holes in the cylinder's wall. Alternatively, the stent may be in the form of a spiral. A stent without fenestrations can also be made according to the method of the present invention using a device which does not have members for defining the fenestrations in the mold space.

FIGS. 2A, 2C, 2E and 2G illustrate four different configurations for a distal catheter body 29 for forming a fenestrated stent. The body 29 functions as a device having a patterned surface 18 with members 19 extending away from the surface 18 for forming fenestrations. The body is advanced within a vessel using a guide wire 35. When used in combination with the interior of a body lumen, the distal catheter body creates a mold for forming fenestrated stents such as those illustrated in FIGS. 2B, 2D, 2F and 2H. Illustrated in FIGS. 2B, 2D, 2F and 2H are cut-away views of vessel lumens 22 where a stent 28 has been formed with fenestrations 39 by the distal catheter body 29.

In a preferred embodiment, the distal catheter body 29 or guide wire 35 used to advance the distal catheter body 29 includes a mechanism for delivering energy to cause or to enhance the rate of conversion of the fluent pre-stent composition to a non-fluent stent composition. The energy delivery mechanism may be designed to deliver one or more different types of energy including but not limited to electromagnetic radiation (RF, microwave, ultraviolet light, visible light, laser), ultrasound, or any other type of energy which can catalyze the transformation of the fluent pre-stent composition to a non-fluent stent composition.

In a particularly preferred embodiment, the energy delivery mechanism is an antenna which provides microwave (MW) energy to the fluent pre-stent composition and converts the fluent pre-stent material to a non-fluent stent composition in situ. The antenna broadcasts microwave (MW) energy into a predetermined volume of space with a predetermined energy density. The antenna system can be located on the distal catheter body. Alternatively, the antenna can be located on a guide wire which passes through the distal catheter body. In this embodiment, the guide wire performs the dual functions of operating as a guide wire and as an antenna. A micro coaxial cable is used to conduct MW energy from a MW generator to the broadcast antenna system on either the distal catheter body or the guide wire.

The distal catheter body 29 also includes an expandable balloon 37 which forms part of the mold cavity. The expandable balloon 37 is in fluidic communication with a reservoir of fluent pre-stent composition proximal to the distal catheter body (not shown). The expandable balloon 37 contains one or more holes or pores 33 for delivering the fluent pre-stent composition into the mold space or cavity through the balloon. The one or more holes may optionally be part of a micro porous membrane (MPM). The diameter of the holes in the expandable balloon optionally expand as a function of the degree of expansion or inflation of the balloon, such that by controlling the pressure applied to fluent pre-stent composition, the diameter of holes in the balloon can be controlled.

Optionally, a second non-expandable (i.e., nonconformal) balloon (not shown) may be included inside the expandable balloon 35. Inflation of the non-expandable balloon with fluid or gas via the multi lumen catheter will apply pressure to the interior wall of the vascular organ, such as is required in angioplasty procedures to break plaque.

3. Method

A method is provided for forming a stent (optionally a fenestrated stent) in a body lumen by the transformation of a fluent pre-stent composition to a non-fluent stent composition in situ. The method can include forming, molding, and/or casting the fluent pre-stent composition into the shape of a stent prior to the fluent—non-fluent transformation using a combination of the body lumen and the catheter distal body. In a preferred embodiment, the method includes advancing a catheter distal body including a balloon to a position where stent deployment is desired. The balloon surface of the catheter distal body provides the compliment to the stent design desired and forms a mold cavity in combination with the intraluminal surface. Once the distal catheter body is advanced to a desired location within the body lumen, the balloon is expanded to form a mold space in combination with the intraluminal surface. Fluent pre-stent material is then translated (i.e., conducted, or pumped, or forced) to the mold space defined by the body lumen and distal catheter body. The fluent pre-stent material is translated to the mold space through the distal catheter body via the catheter. Energy or a chemical catalyst sufficent to cause the fluent pre-stent composition to transform to a non-fluent stent composition is introduced. In a preferred embodiment, a threshold level of microwave energy is applied via an antenna portion of the guide wire located in a central portion of the balloon to transform the fluent pre-stent composition to a non-fluent stent composition. The antenna may alternatively be positioned on the catheter distal body. Once the non-fluent stent composition is formed, the balloon is deflated and the catheter is removed.

Optionally, when a dual balloon catheter composed of an expansible balloon and a nonexpansible balloon, is used, an optional step of inflating the inner non-expansible balloon to contact an artery intimal surface and break any plaque thereon may be interposed between the steps of advancing and initially translating above. In this case, any plaque debris will be preferentially encased in the non-fluent stent material following the transformation of the fluent composition to a non-fluent composition, i.e., a stent.

As illustrated in FIGS. 3A–3G, a fenestrated stent 28 is formed by a catheter 20 by the following steps. As illustrated in the figures, the catheter 20 includes a distal catheter body 29 at which the stent is formed and a hollow tube 31 with a central lumen 33 for delivering the fluent pre-stent composition 26 to the distal catheter body 29 for making the stent. The catheter tube is attached to a supply of the fluent pre-stent composition (not shown). The supply can be located within the body lumen being treated, or outside the body lumen, preferably outside the body entirely. In the later case, the supply can be large and include a mechanical pump for injecting the fluent pre-stent composition, such as, for example, a screw activated piston. The distal catheter body 29 has a patterned surface 18 with members 19 extending from the surface for forming fenestrations. Positioned between the members are pores 33 in the distal catheter body 29 for the delivery of fluent pre-stent material to a mold space defined between the surface 18 and a body lumen 22 in which the catheter body 29 is positioned.

Figure 3A:
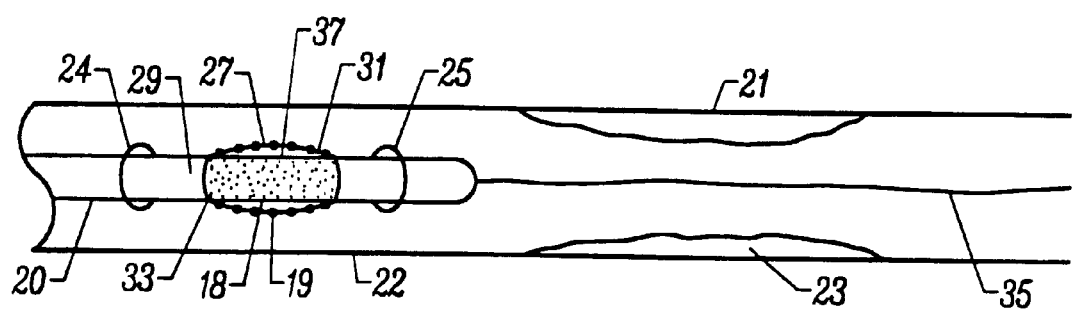
FIGS. 3A–3G illustrate schematic cross section views that depict sequential steps composing a method for making a fenestrated stent, representing an embodiment of the invention.

As illustrated in FIG. 3A, a distal catheter body 29 having a patterned surface 18 with members 19 extending from the surface for forming fenestrations in the in situ formed stent is introduced to a desired region 21 of the body lumen 22. The catheter can be advanced along the path of travel by a guide wire 35 as shown, or by any of various well known methods. As illustrated in FIG. 3A, body lumen 22 is a blood vessel which is partially occluded due to the accumulation of plaque 23 on the lumen walls. The catheter 20 preferably has a flexible, pliant nature and a low coefficient of friction in order to minimize or substantially eliminate trauma to the vessel wall as the catheter 20 is advanced to region 21.

Figure 3B:
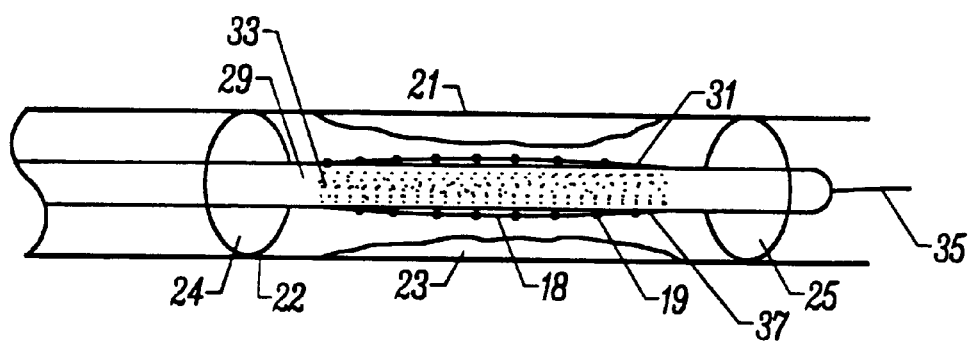
Figure 3I:
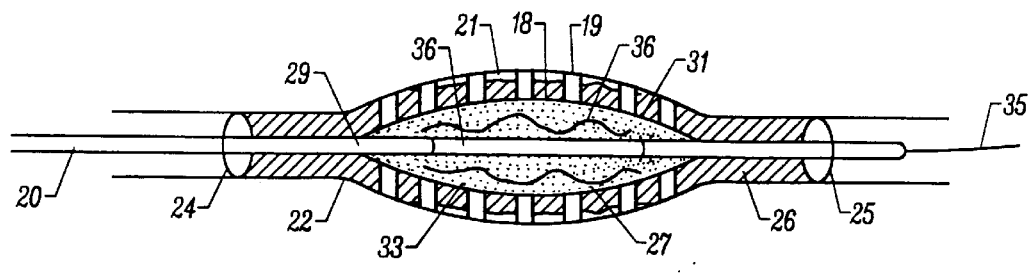
Figure 3J:
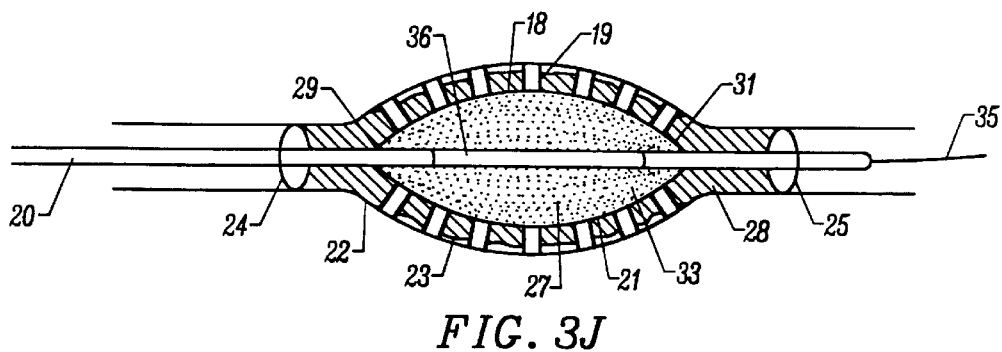
Figure 3K:
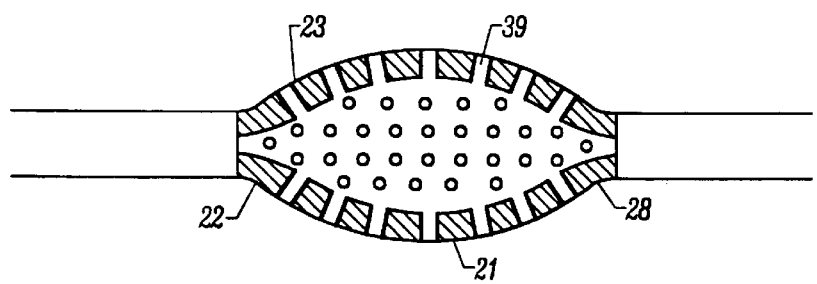

As illustrated in FIG. 3B, the distal catheter body 29 serves to isolate the region 21 of the body lumen 22 and define a cylindrical mold 23 within that region 21 using the lumen 22 as the other mold wall for forming the fenestrated stent. Thus, the lumen 22 defines at least one surface of a mold space. This may be accomplished, for example, by using dual balloons 24, 25 which occlude the lumen 22 both upstream and downstream of the region 21 of the lumen 22 to be isolated. Other mechanisms for isolating region 21 may also be employed. When region 21 is isolated (e.g., fluid flow into and out of the region is prevented), it may be desirable to provide a bypass for the isolated region. This may be accomplished by incorporating a bypass lumen into the catheter body 29.

As illustrated in FIGS. 3C–3D, the distal catheter body 29 may include a central mechanism for expanding the region 21 of the vessel lumen 22. For example, as illustrated, the catheter may include a central balloon 27 for performing balloon angioplasty on the vessel. Other mechanisms for expanding the region 21 of the lumen 22 to be treated may also be used.

Referring to FIGS. 3E–3G, in addition to performing balloon angioplasty and its associated advantages, expansion of the region 21 of the lumen 22 to be treated is desirable with regard to the in situ formation of a fenestrated stent. The fenestrated stent is formed by using the distal catheter body 29 to bring surface 18 near the inner wall of the lumen 22. Members 19 extend from surface 18 of the distal catheter body 29 to define the fenestrations 39. By expanding the distal catheter body 29 prior to stent formation, it is then possible to reduce the size of the distal catheter body 29 after stent formation in order to easily remove the catheter from the body lumen. It is noted that the step of expanding the distal catheter body, as illustrated in FIG. 3D, may be performed before, after, or in combination with the step of introducing a fluent pre-stent material.

As illustrated in FIG. 3E, the fluent pre-stent composition 26 capable of undergoing a transformation to a non-fluent stent composition 28 is introduced into the mold space created by the combination of the distal catheter body 29 and lumen 22. The fluent pre-stent composition 26 is introduced to the mold space via the catheter 20. The fluent pre-stent composition 26 can be transformed to the non-fluent stent composition 28 by a cross-linking or a thermoset activating energy delivery mechanism, such as, electromagnetic radiation (RF, microwave, violet, visible light, laser), ultrasound, or any other type of energy which can catalyze the transformation of the fluent pre-stent composition to a non-fluent stent composition. Alternatively, a chemical catalyst for causing the fluent pre-stent composition to become non-fluent can also be provided. The pre-stent composition 26 can also be provided as a heated thermoplastic. In any event, the fluent pre-stent composition 26 should have the necessary biocompatibility properties.

As illustrated in FIGS. 3E–3G, the distal catheter body 29 includes a balloon 37 with pores 33 through which the fluent pre-stent composition is introduced to the mold space. Once at the site of intervention, the fluent pre-stent composition may be forced outward through the pores 33 by applying pressure to the fluent pre-stent composition within the catheter distal body 29. In this process, the fluent pre-stent composition can be forcibly deposited into any fissures and breaks in the vessel by radial expansion of pores 33.

The balloon 37 of the distal catheter body 29 can include a nonporous membrane having a multiplicity of holes 33 which are laser drilled or pin punched in the surface. The diameter of the holes determines the dispersion characteristics of the fluent pre-stent composition from the membrane. Alternatively, the membrane can be fabricated from a porous material through which the fluent pre-stent composition can be extruded upon the application of pneumatic or fluid pressure to the fluent pre-stent composition. While pneumatic pressure can be used to effect a radial expansion of the fluent pre-stent composition through the holes or pores, it is important that air does not enter the blood vessel. Other types of structures can also be incorporated into the distal catheter body 29 for delivering the fluent pre-stent composition.

In the depicted embodiment, the balloon 37 is a microporous membrane comprising a series of micropores 33 which are small enough to contain the pre-stent composition in a flowable or fluent state. However, the pores are configured such that upon the application of pressure to the internal volume of pre-stent composition contained within the flexible microporous membrane, the pores of the membrane will expand to enable the fluent pre-stent composition to be extruded through the pores and into the mold space surrounding the expanded membrane.

Illustrated in FIG. 3E is an energy source 36 for applying energy to the fluent pre-stent composition. Examples of energies which may be used in the present invention include, but are not limited to electromagnetic radiation (RF, microwave, ultraviolet light, visible light, laser), ultrasound, resistive heating, exothermic chemical heating, or any other type of energy which can heat activate the fluent pre-stent composition.

As illustrated in FIG. 3F, the fluent pre-stent composition 26 is transformed to a non-fluent stent composition 28 which is in the shape of a stent. This transformation may optionally be accelerated by the application of supplemental energy. As shown in FIG. 3F, plaque 23 may be compacted against the wall of the body lumen and may also become encapsulated within the non-fluent stent composition 28. Depending upon the pressure with which the plaque 23 is initially cleared, and the pressure with which the fluent pre-stent material 26 contacts the plaque, the plaque may be intermingled with and incorporated with the non-fluent stent composition 28 as an interphase composite. Alternatively, the plaque can be removed prior to introduction of the fluent pre-stent composition and the formation of the stent. The non-fluent stent composition formed from the fluent pre-stent composition 26 should have the necessary structural and biocompatibility properties for use as a biological stent.

As illustrated in FIG. 3G, after the fluent pre-stent composition is rendered non-fluent, the size of the distal catheter body 29 is reduced so that the catheter may be easily withdrawn from the region of the lumen 22. Meanwhile, the in situ formed fenestrated stent 28 with fenestrations 39 is left in position to structurally support the body lumen 22.

The resulting fenestrated stent 28 should be made of a material that in combination with the fenestration design renders the stent sufficiently rigid to be capable of holding the body lumen 22 in a desired configuration. The fenestrated stent 28 should have a central lumen to allow fluid and biological material to flow through the stent and body lumen 22. The fenestrations should also be sized and positioned to allow fluid and biological material to flow between the body lumen and any vessels that branch from the body lumen 22 in which the stent is formed.

One advantage of the present invention is the ability to have the fluent pre-stent composition to penetrate into fissures in the stenosed tissue. The fluent pre-stent material can be mixed with therapeutic agents to promote healing, such as, for example, growth factors. Other therapeutic agents can also be provided in the pre-stent material to provide a desired therapeutic effect to the vessel. These could include immunosuppressant agents such as cycloporin, adriamycin, and equivalents. Likewise, agents for promoting cell growth of the endothelial tissue may be incorporated into the stent material. Also, a wide variety of well known therapeutically useful pharmaceutical agents may be provided in the stent material for the prevention of restenosis. Examples of such pharmaceutical agents include anticoagulants such as heparin, anti-platelet agents, fibrinolytic and thrombolytic agents as well as anti-inflammatory agents. It will be appreciated that the formation of a stent in situ from a flowable fluent pre-stent material enables heparin or adjuvants for promoting healing to be delivered directly to the injured tissue and to interpenetrate the tissue. The therapeutic agents over time can be bioreabsorbed into the surrounding tissue. The stent composition may also optionally be formed of a bioresorbable material and itself be bioreabsorbed into the surrounding tissue.

In contrast to the invention, a conventional stent is preformed outside a body lumen, such as a blood vessel, and then pushed into place. Thus, there is always some trauma associated with the positioning of the stent. Further, conventional preformed stents do not fill minute fissures and breaks in the injured tissue and thus cannot be used to deliver therapeutic or healing agents to such sites. Additionally, a conventional preformed stent does not conform with the injured or stenosed endovascular tissue. Also, a conventional stent formed outside of the blood vessel does not conform to the unique characteristics or unique configuration of the particular site in the endovascular wall where the stent is to be located.

In preferred embodiments of the invention where the fluent pre-stent composition is introduced via the catheter, the pre-stent composition is protected against contamination from thrombogenic material as it is advanced within the vessel.

It will be appreciated that the fluent pre-stent material lacks sufficient mechanical integrity to form a stent. However, by delivering the pre-stent material in a fluent form to the stenosed region of a blood vessel, trauma to the stenosed region is substantially eliminated as compared to pre-formed stents.

Stenosed tissues are known to be porous or to have numerous fissures. The placement of the fluent pre-stent composition at the site of a stenosed blood vessel provides the advantage of substantially eliminating the trauma normally associated with the placement of a rigid stent. The introduction of pre-stent composition in a fluent state provides a further advantage of being able to penetrate fissures and other breaks and unconformities in injured endovascular tissue with the pre-stent material. In addition, the fluent pre-stent composition interpenetrates the narrow fissures and openings in the endovascular wall and forms an interlinked, anchoring structure which holds the stent firmly in place once it is solidified and the angioplasty balloon is removed.

In one particular embodiment of the catheter, illustrated in FIG. 4A, the catheter 20 includes a guide wire 35 which includes a microwave antenna 39 for delivering microwave energy. The guide wire 35 may be slidable relative to the catheter body. Alternatively, the microwave antenna can be fixed relative to the catheter so that the catheter and the antenna slide on the guide wire. In either case, the fluent pre-stent composition 26 preferably includes a composition 40 capable of absorbing microwave energy and thus can be used to heat the fluent pre-stent composition 26.

In another embodiment, illustrated in FIG. 4B, an RF energy source 100 is coupled through a catheter tube 108 to an electrode 102 at a distal catheter body. Preferably, the electrode 102 has a metallized or conductive microporous surface 104 (e.g., a metallized balloon) for conducting RF energy (shown by arrows) into adjacent fluent pre-stent material.

In yet another embodiment, illustrated in FIG. 4C, the fluent pre-stent material includes a photo initiator or photo polymer material which is changed from a fluent state to solid state upon the application of optical energy of a predetermined intensity, such as ultraviolet (UV) light of a predetermined wavelength, to effect polymerization for the change of the fluent pre-stent material to a non-fluent state. According to this embodiment, a source of optical energy 124 is conducted to the hollow catheter 108 through a fiber optic cable 126 in accordance with techniques which are well known. A conventional optical emitter 128 is positioned within the distal catheter body for irradiating the surrounding pre-stent composition with a source of optical energy necessary to achieve photo polymerization in accordance with techniques which are well known. The optical energy from the emitter 128 irradiates the surrounding pre-stent material equally and effects a substantially complete polymerization and solidification of the stent material about the distal catheter body which acts as a mold surface. Alternatively, the optical emitter 128 may comprise any conventional mechanism for emitting optical energy of a predetermined intensity to effect photo polymerization. For example, the emitter 128 could be a microlens integrated onto a surface emitting laser. The microlens, as in the case of a conventional optical emitter, may be disposed within the balloon 120 and can be irradiated by a collimated beam from a conventional laser through a fiber optic cable.

FIG. 4D shows an alternate method for applying activation energy to the fluent pre-stent material. In this embodiment, an expandable, flexible catheter tube or balloon 140 comprises a microporous surface 142. A quantity of fluent pre-stent material is placed in the hollow catheter tube 140 and is extruded through the microporous surface 142 by the application of pneumatic or fluid pressure. An electrical source 144 is coupled through catheter tube 108 to a piezo electric crystal or ultrasound emitter 150 which is positioned within the expandable microporous catheter tube 140. The piezo electric crystal or ultrasonic transducer 150 is activated in accordance with techniques which are well known to apply an activation energy shown by the arrows in FIG. 4D to the pre-stent composition which has been extruded through the microporous surface 142.

Figure 4E:
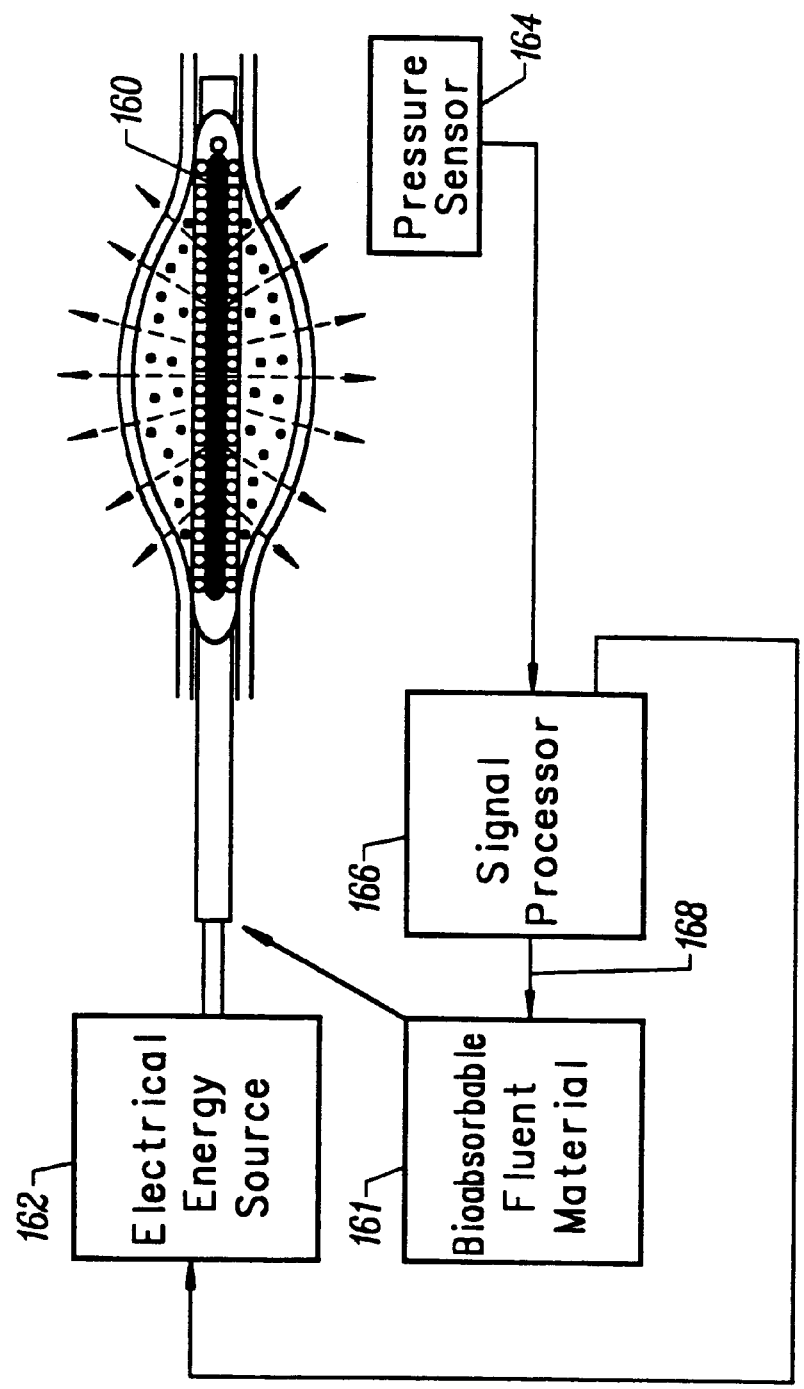
FIG. 4E illustrates a schematic diagram of a system for adaptive feedback and automated control of a method for applying energy to cure a fluent pre-stent material, representing an embodiment of the invention.

As illustrated in FIG. 4E, a resistive heating element 160 for heating the fluent pre-stent composition may also be incorporated into the catheter. Once a sufficient amount of fluent pre-stent composition has been delivered from a fluent pre-stent composition source 161, a source of electrical energy 162 activates the resistive heating element 160. The heat energy from the resistive heating elements 160 is conducted radially outward to the fluent pre-stent composition and causes the fluent pre-stent composition to be transformed into a nonfluent stent composition. According to this aspect of the invention, resistive heating may also be accomplished through a distributed array of malleable resistive heating elements provided over the distal catheter body in accordance with techniques which are well known. An array of resistive heating elements may be deposited, laser welded or otherwise provided over the outer surface of the balloon. This would have the advantage that the heating elements would be in direct contact with the mold surface formed by the distal catheter body and thus could provide direct and immediate conduction of heat energy to the pre-stent composition.

Adaptive feedback may be used to closely control the delivery of pre-stent composition through the catheter to the vessel. The source of fluent pre-stent composition 161 includes a composition capable of effecting a change of state upon the application of energy above a predetermined threshold. This source of composition 161 can be completely contained within the distal catheter body. Alternatively, the source of composition 161 can be provided from a chamber or reservoir that is located external to the distal catheter body. In the latter case, the composition can be delivered to the distal catheter body through a line interconnecting the chamber or reservoir to the distal catheter body.

The amount of fluent pre-stent composition which is introduced into the vessel lumen may be controlled by an active feedback control system. For example, a microelectronic pressure sensor 164 may be disposed within the catheter for adaptive feedback control of the amount of fluent pre-stent composition to be passed through the catheter into the vessel lumen. The adaptive feedback control helps to ensure that the fluent pre-stent composition is evenly distributed as it is cast against the lumen wall. Known feedback methods are then used to control the amount of fluent pre-stent composition that is flowing through the catheter. The object is to equalize pressure over the surface of the distal catheter body to a predetermined threshold which would be compatible with expanding the fluent pre-stent composition into fissures in the surrounding lumen wall without damaging any endovascular tissue. Once the predetermined pressure is reached, signals from the pressure sensor 164 are provided to a signal processor 166 for amplification in accordance with techniques which are well known. The amplified signals 168 from the signal processor 166, indicative that the predetermined pressure has been reached, are then provided to the source of pre-stent composition 161 in order to block further introduction of pre-stent composition into the system. Also, signals 168 from the signal processor 166 may be applied to the electrical energy source 162 to activate the resistive heating element 160 and initiate delivery of energy to the pre-stent composition. This also has the effect of preventing additional pre-stent composition from entering the vessel. The adaptive control system also prevents overexpansion of the distal catheter body and prevents excess pre-stent composition from entering the vessel.

FIGS. 5A and 5B show two alternate systems for advancing a catheter 100 to a desired region of a body lumen. Illustrated in FIG. 5A is a guidewire system for advancing a catheter along a path of travel in a typical blood vessel. A guidewire 102 is threaded through the catheter 100. The proximal end of catheter 100 is attached to a hollow catheter tube 104 for the introduction of a fluent stent composition into the catheter 100 as will be explained. The guidewire 102 is adapted to advance the catheter 100 along a path of travel within the vessel.

FIG. 5B shows an alternate steerable system in which a porous catheter 100 is attached to a steerable catheter tube 105. The steerable catheter tube 105 comprises a distal and with a steering element 107. The proximal end of catheter tube 105 is connected to a source of fluent stent material for delivery to the porous catheter 100 in accordance with techniques which are well known. In this system, the catheter 100 is advanced along a path of travel in a blood vessel by pressure applied to catheter tube 105. A steering element 107 can be a shape memory alloy activated device or other conventional steering device which enables the application of torque for steering catheter 100 in a particular direction when a junction is reached.

Figure 6B:
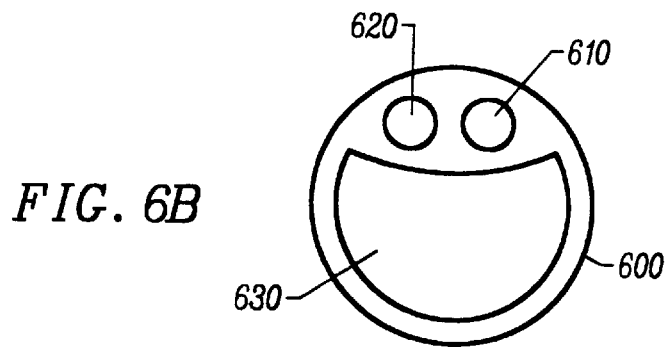
FIG. 6B illustrates a cross-sectional view of the device depicted in FIG. 6A.
Figure 6A:
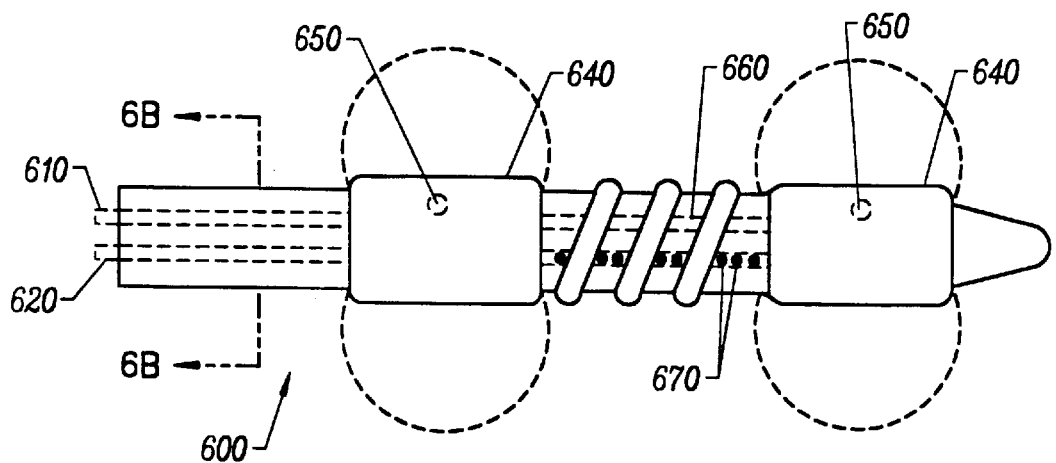
FIG. 6A illustrates a side view of a device for making a spiral fenestrated stent, representing an embodiment of the invention.

FIGS. 6A and 6B depict a catheter 600 for molding a spiral-shaped fenestrated stent in situ. The catheter 600 provides a portion of the surface area of a mold space defined between the catheter 600 and a tubular organ in which the catheter 600 is located.

FIG. 6A shows the device in both collapsed form and with a pair of occluding balloons 640 expanded (phantom lines). A balloon inflation lumen 610 conducts a liquid inflation medium to the balloons 640 through a pair of passageways 650. A fluent pre-stent composition lumen 620 conducts the fluent pre-stent composition to the mold space. The fluent pre-stent composition can reach the mold space through a plurality of microporous holes located in those portions of a central section 660 that are located in between the raised fenestration rib 670, or, the fluent pre-stent composition can reach the mold space through a plurality of macro-porous holes 670 that are directly connected to the fluent pre-stent composition lumen 620. In the former case, the interior of the control section 660 is filled with composition via holes 670 and the composition then passes from the interior of section 660 to the mold space via the microporous holes. Section 660 can be separately inflatable.

FIG. 6B shows a cross-section of the device taken upstream of the first balloon. The device includes three lumens at this point. A balloon inflation lumen 610 carries a medium to expand the balloons of the device and occlude the body lumen. A pre-stent composition lumen 620 conducts the composition that will be cast adjacent the living tissue. The device also includes a guide wire lumen 630 through which a guide wire is passed. In this embodiment, the guide wire lumen 630 provides a conduit for an RF power source in addition to encasing the guide wire that directs the device 600.

Figure 7:
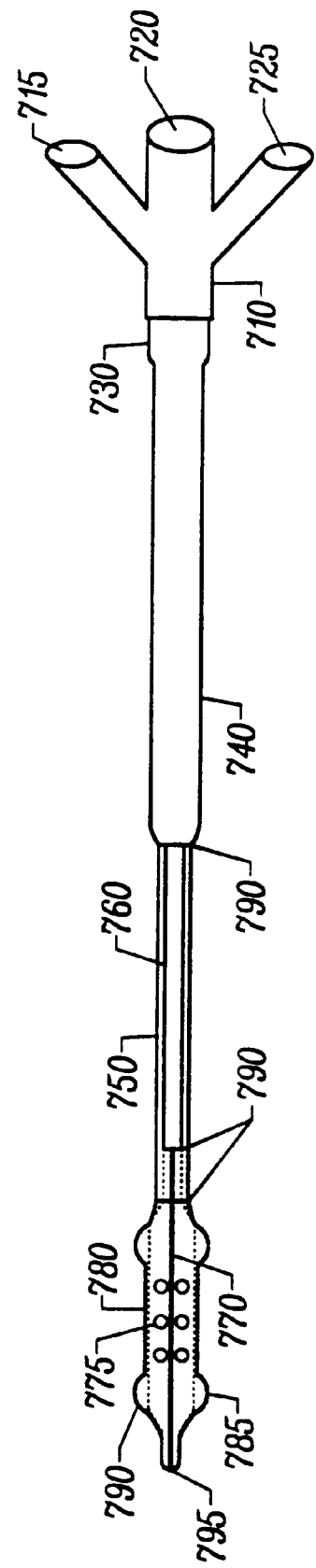
FIG. 7 illustrates side, a partial sectional view of a device for forming a stent, representing an embodiment of the invention.

FIG. 7 shows a preferred device for forming a fenestrated stent in situ. A molded three-arm lure adaptor 710 includes a slurry lumen 715, a contrast/guide wire port 720, and a balloon inflation lumen 725. Proceeding downstream, the device includes a strain relief apparatus 730 such as a swivel bearing, bellows, plastic coupling, or other means for relieving strain between the adaptor and the rest of the apparatus.

Still referring to FIG. 7, the device includes proximal outer shaft 740. The proximal outer shaft 740 can be made of high density polyethylene. The proximal outer shaft 740 is connected to a distal outer shaft 750. The distal outer shaft 750 can be made of low density polyethylene. Located within both the proximal outer shaft 740 and the distal outer shaft 750 is an inner shaft 760. The inner shaft 760 can be made of low density polyethylene. In preferred embodiments, the outer diameter of the proximal outer shaft 740 is less than 3.5 f. In preferred embodiments, the outer diameter of the distal outer shaft 750 is less than 3.3 f. An inner member 770 is located within the inner shaft 760. The inner member 770 can be a heavy duty nylon material, or any other material, suitable for use as a guide wire lumen. A guide wire (not shown) can be threaded through the member 770. At the distal end of the inner shaft 760, a dual balloon 780 is held at one end. The mechanical junction between the outer shafts 740 and 750, as well as the junction between the outer shaft 750 and the balloon 780, as well as the end of the inner shaft 760 can all be transition points composed of lap joints 790. The balloon 780 includes an outer balloon 785. The outer balloon 785 is a peanut shaped conformal balloon. The functions of the outer balloon 785 are to occlude the lumen and provide an inner mold surface. The expanded shape of the outer balloon 785 is shown in solid lines while the non-expanded shape (during insertion, positioning, and withdrawal) is shown in phantom lines. The outer balloon 785 can be coated with gold. Within outer balloon 785 is an inner balloon 790. The inner balloon 790 is a non-conformed balloon. The function of the inner balloon 790 is to break plaque. The inner member 770 passes through the middle of both inner balloon 790 and outer balloon 785 exiting at a nose 795. The outer balloon 785 is provided with a plurality of fluent pre-stent material lumen terminations 775 through which the fluent pre-stent composition can flow so as to fill a mold space defined in part by the expanded outer balloon 785. The fluent pre-stent composition can be provided to the terminations 775 through a plurality of individual lumen (not shown) or through a central manifold (not shown).

FIGS. 8A and 8B show a double balloon structure 800 with an outer balloon 810 including a laminated RF electrode membrane. An inner non-porous angioplasty balloon 820 is located within the outer balloon 810. FIG. 8A shows fluent pre-stent composition 805 being directed into the outer balloon 810 and flowing through pores 825 in the outer balloon 810. The fluent pre-stent composition is provided through a lumen 812 via holes 815. The structure is threaded onto a guidewire 880 which can be distal the area to be treated.

FIG. 8B shows the laminated RF electrode membrane 810 in more detail. An inner insulating layer 830 may be considered as a substrate for a conductive layer 840 which is sandwiched between a top insulating layer 850 and the inner insulating layer 830. All three layers are provided with through holes 860 for porosity. It should be noted that the top insulating layer 850 is provided with openings 870 coaxial with the through holes 860 for exposing the conductive RF layer. In this way, RF radiation 880 from the electrode is directed out from the balloon structure 800 toward the mold space. Relatively little RF radiation from the electrode emanates inward (toward the inner balloon).

Figure 9:
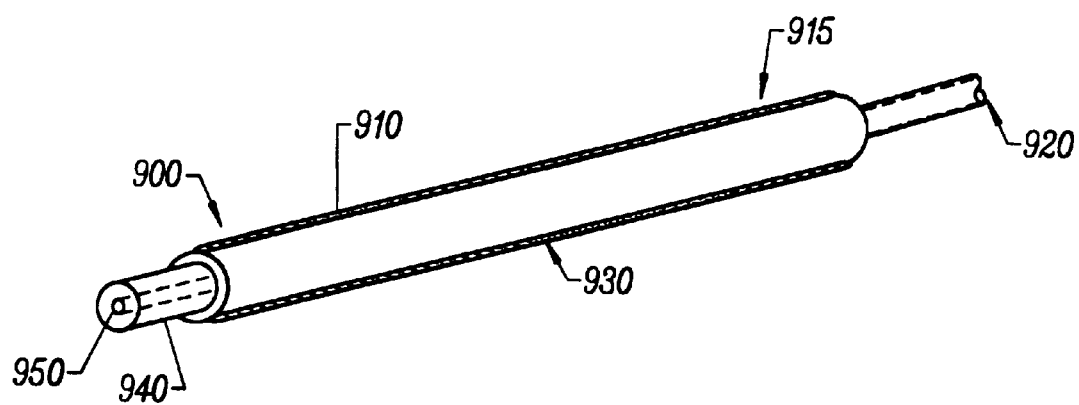
FIG. 9 illustrates a perspective, partial section view of a device for forming a stent, representing an embodiment of the invention.

FIG. 9 shows a catheter 900 for forming stents of variable lengths. Two independent microporous membrane covered balloons (920, 930) are arranged concentrially one inside the other. By sliding the balloons relative to each other, a variable length stent may be cast.

FIGS. 10A and 10B show the distal catheter body 1060 of a catheter system having profusion valves and a bypass lumen. Blood flow 1000 through the body lumen 1050 and the distal catheter body 1060 is from left to right.

FIG. 10A depicts the distal catheter body 1060 in a collapsed (non-expanded) condition with proximal and distal profusion valves 1010,1011 closed. In this configuration blood is free to flow around the distal catheter body and through the body lumen 1050.

FIG. 10B depicts the distal catheter body in an expanded condition. In this configuration blood flow within the body lumen 1050 around the distal catheter body 1060 is blocked. Upon expansion of a balloon 1020, the proximal and distal profusion valves 1010,1011 open. These valves are interconnected by a bypass lumen (not shown) which allows blood entering the open proximal valve 1010 to flow past the distal catheter body via the bypass lumen and out the distal valve 1011. While blood flows through the profusion valves, a fluent pre-stent composition is introduced into the mold space 1030 through a plurality of holes 1040. The plurality of holes 1040 formed in the balloon 1020 and connect the mold space 1030 to a fluent pre-stent composition lumen located within the catheter. After being introduced into the mold space 1030, the fluent pre-stent composition is transformed to a non-fluent stent composition, for example by curing the pre-stent composition with radio frequency energy or microwave energy. The particular pre-stent composition used will depend on the particular fluent—non-fluent transformation to be performed and the particular form of energy used.

Figure 11:
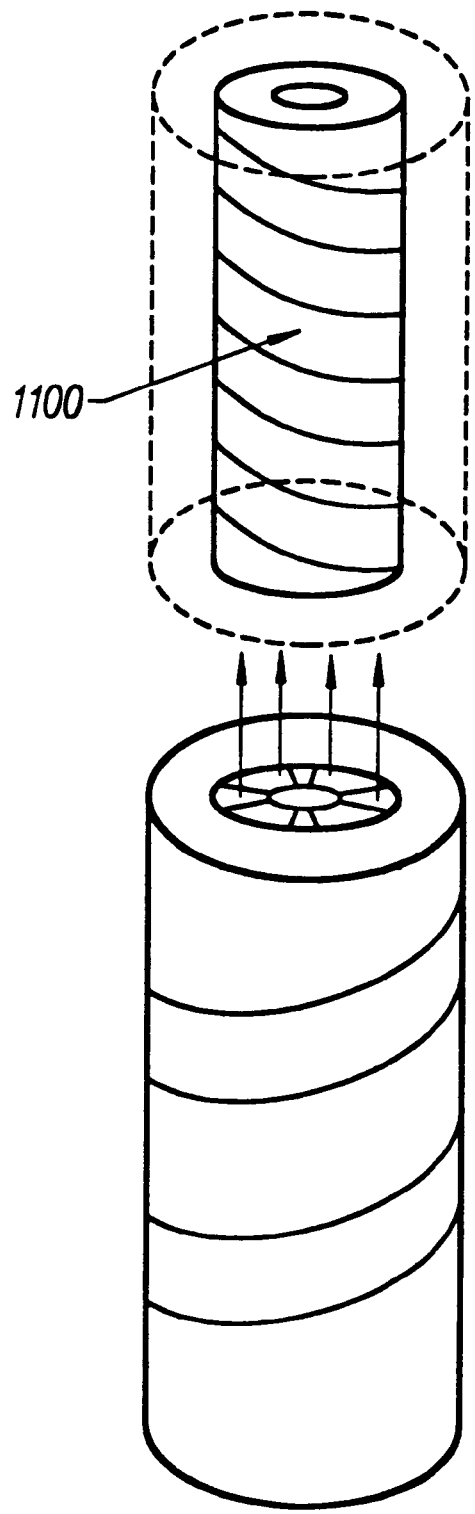
FIG. 11 illustrates a perspective partially exploded view of a device for forming a stent, representing an embodiment of the invention.

FIG. 11 depicts a perfusion valve which allows blood flow while the balloon is expanded.

Figure 12A:
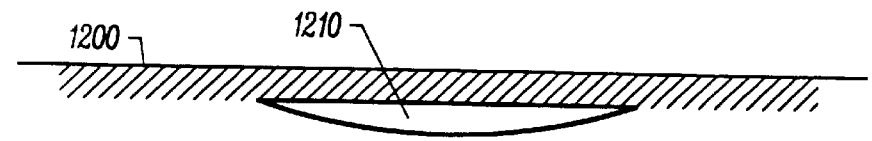
FIGS. 12A–12F illustrate schematic sectional views that depict sequential steps composing a method for breaking plaque and forming a stent, representing an embodiment of the invention.
Figure 12B:
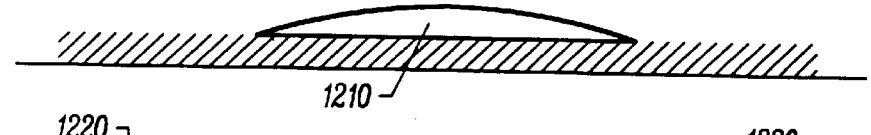
Figure 12C:
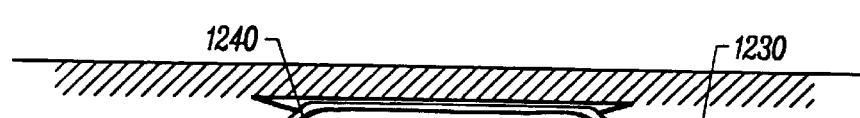
Figure 12D:
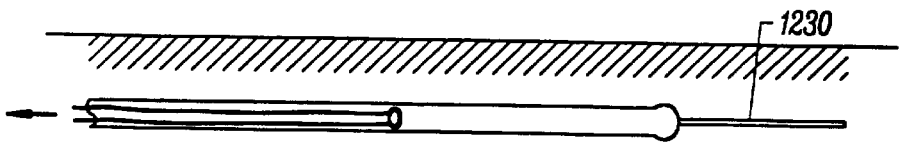
Figure 12E:
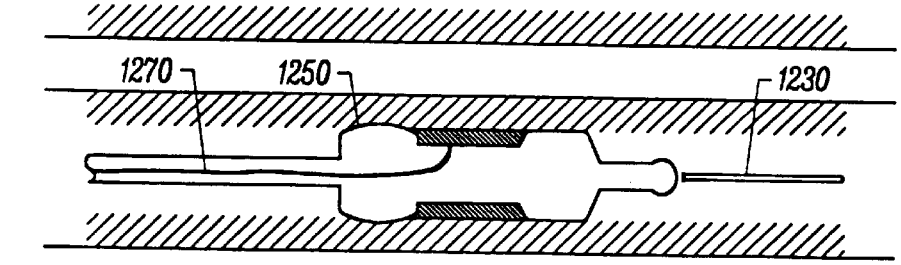
Figure 12F:
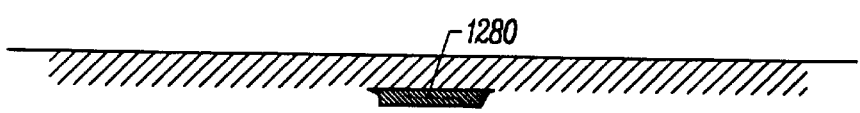

FIGS. 12A–12F illustrate a particular embodiment of the device and method of the present invention. As illustrated in this sequence, a device having a noncompliant interior balloon and an outer elastic (compliant) balloon is used to form a stent in situ. FIG. 12A depicts an occluded blood vessel 1200. FIG. 12B depicts a distal catheter body 1220 advanced across the occlusion. Distal catheter body 1220 is positioned on a guide wire 1230. FIG. 12C depicts a noncompliant interior balloon 1240 inflated to achieve dilation of the blood vessel 1200. FIG. 12D depicts the interior noncompliant balloon 1240 deflated and being withdrawn to the left out of balloon 1250 (arrow pointing to left). FIG. 12E depicts an outer elastic (compliant) balloon 1250 inflated to form a mold 1260 in which the fluent pre-stent composition is injected through a lumen 1270 that is attached to the surface of the elastic balloon 1250. FIG. 12F depicts a finished stent 1280 formed by the conversion of the fluent pre-stent composition (delivered in the step depicted in FIG. 12E) to a non-fluent stent material.

FIG. 13 depicts an in situ formed stent according to the present invention which has a desired degree of porosity, i.e., the stent includes a plurality of pores or holes in the wall of the stent which allow objects such as molecules, materials, cells, aggregates of a desired size range to traverse the stent. The pores in the stent may optionally be sufficiently large to allow any object normally found in the blood to traverse the stent. The stent 1300 includes a first end 1310, a second end 1320, and a cylindrical microporous wall 1330. The wall 1330 includes a plurality of micropores.

The micropores can be provided in several different ways. One way of providing the micropores is to include a component in the fluent pre-stent composition which gets bioresorbed at a different, faster rate than the stent, leaving behind a network of channels where the component was dispersed in the stent when the stent was formed. This bioresorbable material can optionally be a therapeutic agent which performs a therapeutic function in the process of being resorbed by the body. Another way in which the micropores can be provided in the stent is to include a foaming agent in the fluent pre-stent material. The foaming agent can be either a gas or a liquid. The action of the foaming agent creates the micropores. Alternate ways of forming a porous polymeric material are also known in the art and are intended to fall within the scope of this invention.

FIG. 14 provides an expanded cross section of the wall 1330 of the stent illustrated in FIG. 13. The wall 1330 is adjacent a vascular wall 1400. The wall 1330 is also adjacent a flow of blood 1410. The principal flow of the blood is depicted by the large arrowhead. In addition, blood and other materials can flow through the wall 1330 in either direction as depicted by the three curvaceous arrowheads. Nutrients in the blood 1410 can leach through the open cell structure of the wall 1330. Alternatively, the wall 1330 can supply necessary nutrients, proteins, cells and other biological materials to the inner surface of the stent through the wall.

FIGS. 15A and 15B illustrate a stent fabricated to include electrodes. This stent can be used to promote electrolysis can be used to prevent platelet and/or macroflange attachment. As illustrated in FIG. 15A, a bimetal stent can be constructed so as to exhibit an electrolysis effect. A first metal 1510 is placed in a spaced apart arrangement from a second metal 1520. If the electrolytic reduction potentials of the metal are sufficiently different, a voltage potential will be generated between the two metals.

FIG. 16B illustrates a composite stent constructed to contain electrically active materials. If the electrically active materials are separated from one another, such a stent can be used to act as a battery emitting a slight electrical charge to prevent platelet attachment.

FIGS. 16A–16G illustrate a method for forming a fenestrated stent or a stent containing macropores in situ by including a separate phase in the stent that can be bioresorbed faster than the remainder of the stent. When the separate phase is resorbed, fenestrations or macropores are created in the stent where the separate phase existed and has been removed.

FIG. 16A illustrates a stent 1610 having a generally corkscrew design. This stent can be formed by the catheter illustrated in FIG. 16B. As illustrated in FIG. 16B, the catheter 1620 is connected to a guidewire 1625. The catheter 1620 includes a stent forming balloon 1630. The stent forming balloon 1630 includes a plurality of holes 1635 through which fluent pre-stent material can be exuded. A stretchable, dissolvable core 1640 is carried on the surface of the balloon 1630.

Use of the catheter illustrated in FIG. 16B to form the stent illustrated in FIG. 16A is illustrated in FIGS. 16C–16G. As illustrated in FIG. 16C, the catheter illustrated in FIG. 16B is inserted into a tubular organ. The stent forming balloon 1630 is then expanded as illustrated in FIG. 16D. FIG. 16E shows an expanded cross section of a portion of the balloon depicted in FIG. 16D. The core 1640 is adjacent to a wall 1650 that includes a surface of living tissue. A fluent pre-stent material 1655 is extruded through the holes 1635. The fluent pre-stent material is then rendered non-fluent to form the stent. As illustrated in FIG. 16F, after the balloon 1630 is deflated and the device 1620 removed, the core 1640 and the cast stent material 1655 remain adjacent the wall 1650. After the core material 1640 is resorbed, the stent illustrated in FIG. 16G remains.

FIGS. 17A–17D illustrate a device 1700 for forming a fenestrated stent which includes a flexible removable mold core 1710. When the balloon of device 1700 is expanded, the mold core 1710 expands against the intima of the vessel in which it is located. Fluent pre-stent composition is then exuded through the holes in the balloon and converted in situ to a non-fluent stent composition. After the balloon is deflated, the balloon is removed, providing a central void through which the flexible removable mold core 1710 can be peeled away. In the depicted embodiment, the proximal end of the mold core 1710 is tethered to the distal end of the balloon. Referring to FIG. 17D, a fenestrated stent 1730 remains after the mold core 1710 is removed.

Figure 18A:
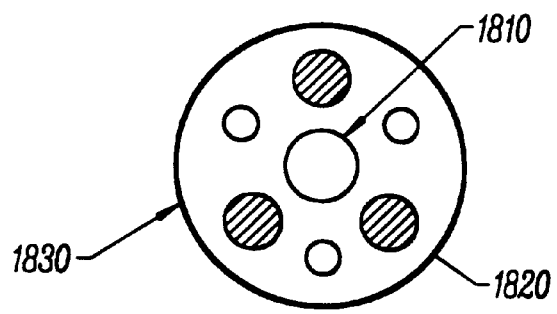
FIG. 18A illustrates a schematic sectional view of a device for forming a stent, representing an embodiment of the invention.
Figure 18B:
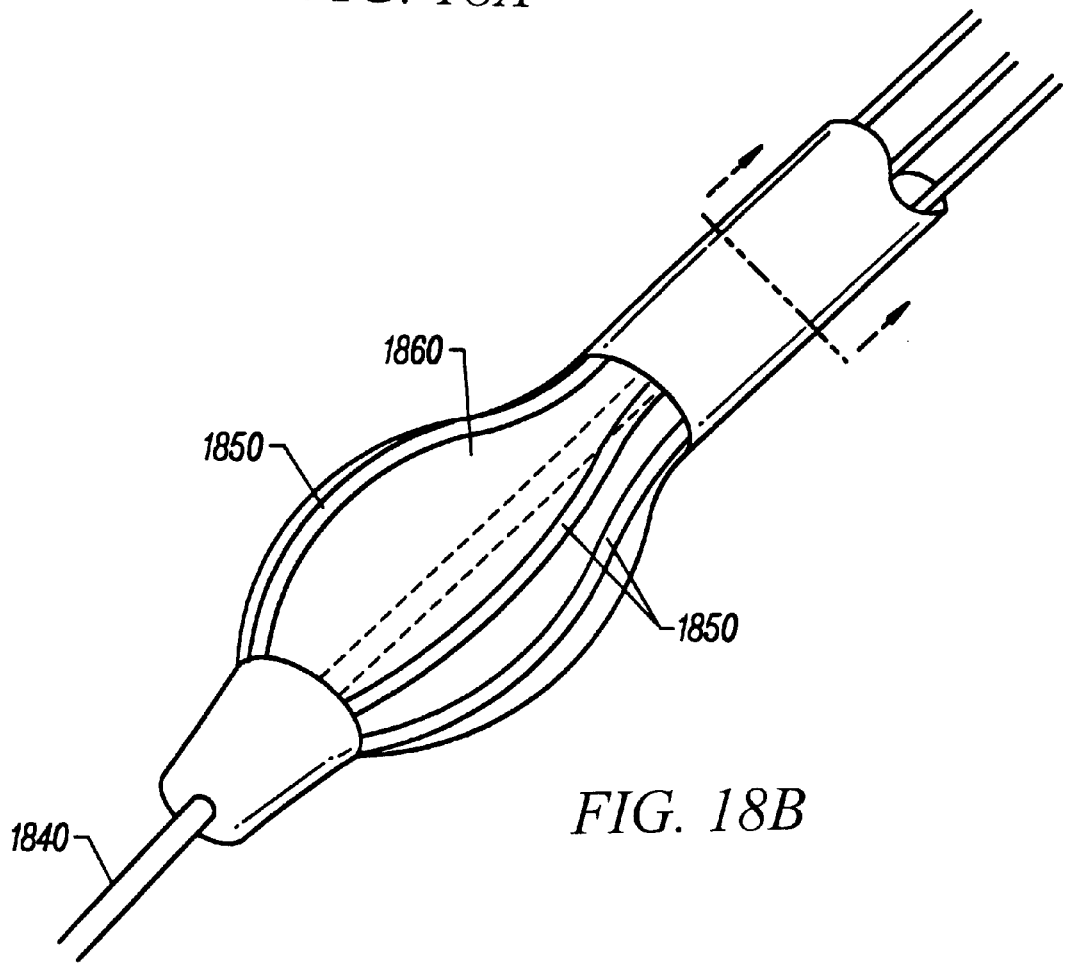
FIG. 18B illustrates a schematic perspective view of a device for forming a stent, representing an embodiment of the invention.

FIGS. 18A–18B illustrate embodiments of a catheter where electromagnetic energy for converting the fluent pre-stent composition to the non-fluent stent composition is provided through a plurality of wave guides. This permits delivery of a higher amount of power to the distal end of the stent forming device. The wave guides can be microwave coaxial minicables. FIG. 18A provides a cross section of the device. The device includes a guidewire channel 1810. The device also includes three microwave channels 1820. In addition, the device includes three fluid/inflation ports 1830. FIG. 18B provides a prospective view of the device depicted in FIG. 18A is illustrated. The device is threaded on a guide wire 1840. In the depicted embodiment, the microwave mini-coaxial cables 1850 are embedded in a balloon 1860.

Figure 19A:
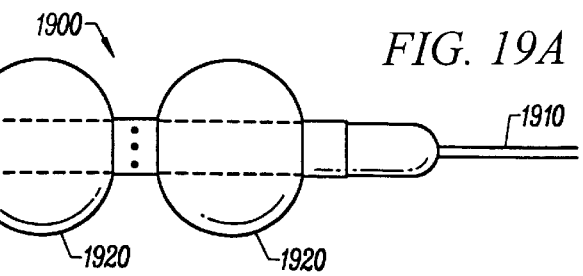
FIGS. 19A–19D illustrate schematic views of a device for forming serial stents, representing an embodiment of the invention.

FIGS. 19A–19D illustrate the operation of a device for simultaneously forming a plurality of stents. The stents are serially arranged along the longitudinal axis of a tubular organ and spaced apart by occluding balloons. FIG. 19A illustrates a device 1900 mounted upon a guide wire 1910. The device includes a plurality of occluding balloons 1920. The balloons 1920 are depicted in an expanded state in FIG. 19A.

Figure 19B:
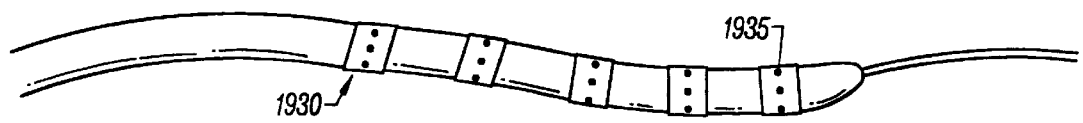

Turning to FIG. 19B, the balloons 1920 are depicted in a deflated state. The balloons 1920 are separated by metal rings. The proximal metal ring 1930 and the distal metal ring 1935 are non-perforated. The intermediate metal rings 1940 include a set of perforations through which fluent pre-stent material is extruded when the balloons 1920 are expanded and occluding the tubular organ in which the stents are to be located. The balloons can be made of a silicone/elastomer.

Figure 19C:
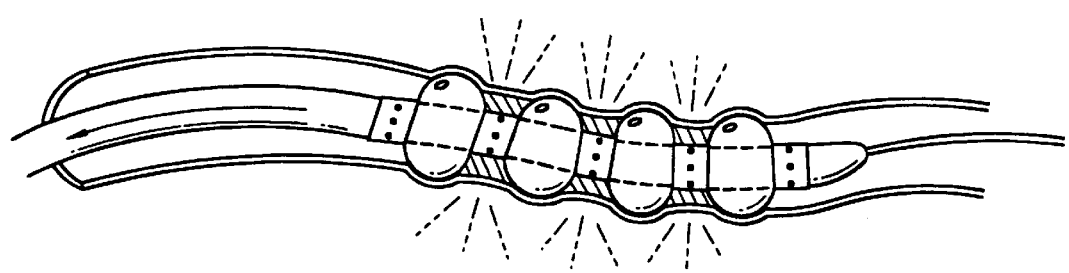
Figure 19D:
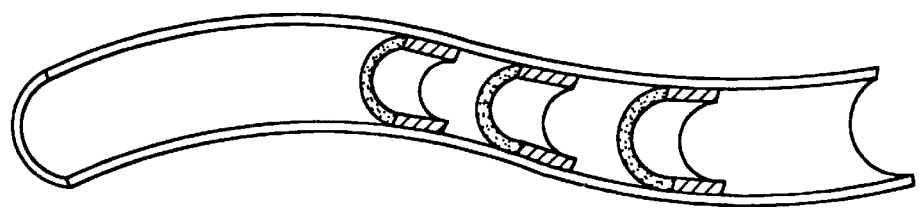
Figure 20:
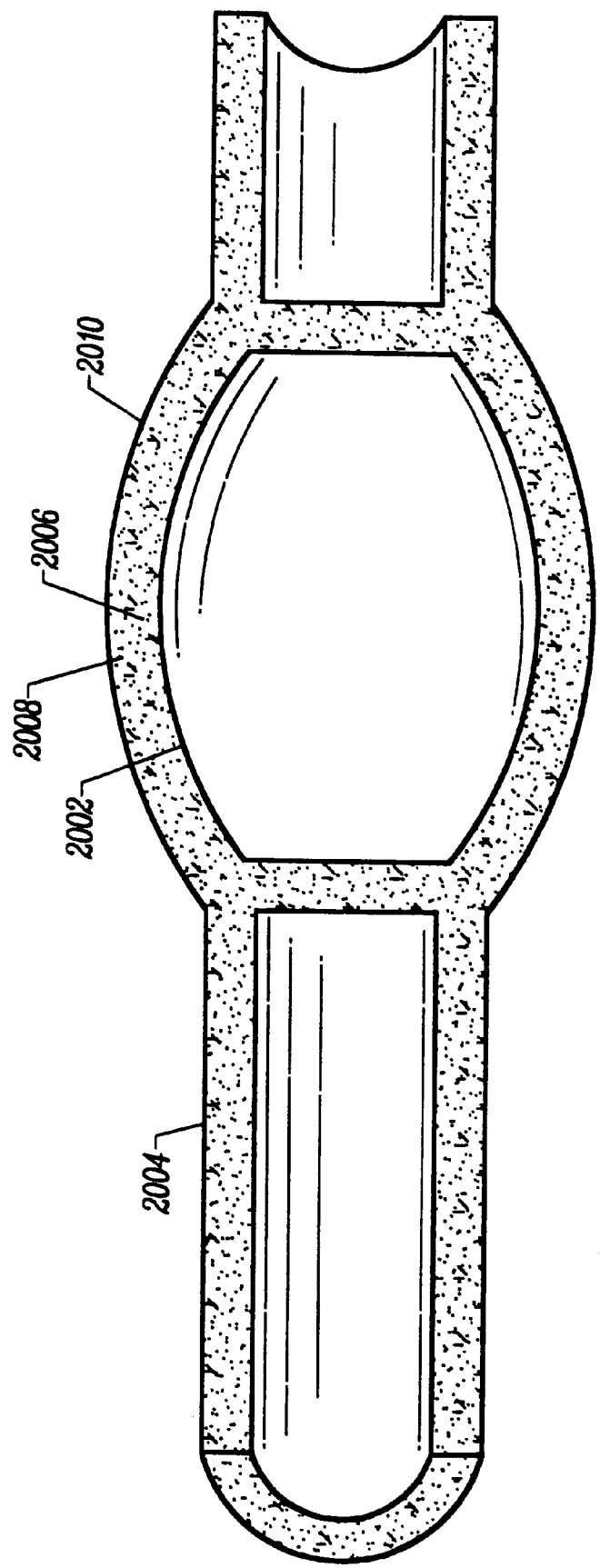

Turning to FIG. 19C, the device 1900 is depicted in an expanded state as it occludes a tubular organ. A fluent pre-stent composition is deposited through the holes in the metal rings and electromagnetic energy (e.g., RF, MW, UV) is delivered to the deposited material. Referring to FIG. 19D, three finished stents are shown to be formed adjacent the tubular organ.

4. Compositions

Compositions that can be converted from a fluent state to a nonfluent state have found general utility across industry groups. One mechanism for this conversion is via a free radical or cationic polymerization reaction. Such reactions often rely on a specific chemical composition to initiate the polymerization which are commonly called "initiators". For example, for thermal free radical polymerizations, compositions containing peroxy (—O—O—) or azo (—N=N—) functionality are often used; for photochemical free radical polymerizations compounds such as benzoin ethers are often used; for thermal cationic polymerizations, compounds such as mineral acids are often used; for photochemical cationic polymerizations, compounds such as triphenyl sulfonium hexafluorophosphate are often used.

In many thermosetting systems, two properties of the initiator are desired simultaneously: 1) a reasonable shelf-life or pot-life at a first lower temperature and 2) a rapid reaction rate at a second higher temperature. An initiator with such properties has been termed a "latent initiator" or a "latent catalyst", and the difference between the first lower temperature for inactivity and the second higher temperature which activity occurs is called the "temperature window". While photochemical initiators possess an innate degree of latency since they become active only in the presence of light, in homogeneous systems, thermal initiators are bound by the constraints of finite reaction rates even at low temperatures. In general, the rate of change of a chemical reaction, including the initiator reaction and subsequent polymerization reactions contemplated here, are governed by the Arrhenius equation:

ln (rate constant)=(Constant)*$e^{(-E_{act}/RT)}$ where $E_{act}$ is the energy of activation, R is the gas constant, and T is the temperature in degrees Kelvin. Typical initiation reactions have $E_{act}$ values from 12–20 kcal/mole. In applying such values to the Arrhenius equation, it will be seen that if the allowed difference in temperature is only of the order of 20° C., as is the case here where the material will be stored at 25° C. and used at about 45° C., then the difference in cure or setting times for a composition will be only about a factor of 4–8 times. Consequently, if a setting time of 2 minutes or less is desired, the pot-life of the composition will necessarily be at most 8–16 minutes, which is too short.

A latent initiator system with a smaller temperature window that is inactive or minimally active at a first lower temperature but becomes active at a second, higher temperature that is relatively closer to the first temperature than in prior systems can be based on the following composition: The composition includes an energy susceptible material, preferably a solid, and a layer of a polymerization initiator surrounding and coating the energy susceptible material. Optionally, the composition can include a second layer surrounding and coating the first layer of a material that has a phase transition, preferably a melting point, such that said transition occurs over a temperature range of no more than 5° C. and after completion of the phase transition allows communication between the initiator material and the bulk material to be polymerized.

This approach has several advantages over currently known latent initiators. First, because the thermal energy is preferentially introduced into the core energy susceptible material, the instantaneous temperature at the core can be higher than that of the bulk composition. Since the polymerization initiator is in contact with the core, it may begin rapid initiation of polymerization while the bulk temperature is still too low a temperature for a rapid reaction.

Second, when the optional second layer is employed, the initiator effectively will be protected from contact with the material to be polymerized by the crystalline structure of this outermost layer; hence the pot-life and/or shelf-life of the composition will be improved. When the melting temperature is reached, a sharp phase transition will occur over a narrow temperature range which will then allow initiation and curing to commence as the heated initiator comes into contact with the polymerizable composition.

Preferably, the core energy susceptible material will be strongly interactive with microwave (MW) electromagnetic radiation. In this case, energy will be efficiently coupled directly to the core of the latent initiating particle without much heating of the surrounding material to be cured. The absorbed energy will quickly be released as heat, suitable for beginning thermal initiation and the phase transition of the outer layer. Suitable core materials are: ferric oxides, ferrites, graphite, amorphous carbon, lamp black, grey iron, iron, metals, ferrosilicons, solid polymer electrolytes. Suitable initiators are peroxides and azo compounds. Suitable phase transition materials are poly(ethylene oxides), main chain liquid crystal polymers, side chain liquid crystal polymers, poly(esters) such as poly(trimethylene glutarate), poly(trimethylene suberate), poly(trimethlyene adipate), poly(ethers) such as poly(tetrafluoroethylene oxide). Examples of particular iron oxide materials that can be used include, but are not limited to hematite ($\alpha$-$Fe_2O_3$), maghemite ($\gamma$-$Fe_2O_3$), magnetite ($Fe_3O_4$), geothite ($\alpha$-FeOOH), lepidocrocite ($\gamma$-FeOOH), ferrihydrite, feroxyhyte ($\delta$-FeOOH), akageneite ($\beta$-FeOOH) graphite and amorphous carbon. The microwave absorptive composition that constitutes a constituent of the fluent pre-stent material can be tantalum containing materials such as reduced metallic tantalum and/or tantalum oxides.

A fluent pre-stent composition can be converted from a fluent to a non-fluent state by application of a threshold level of microwave energy. Additionally, the frequency of the MW energy can be specified or tuned to more effectively transfer energy to specific components of the composition. The ultimate result of such an energy transfer mediated by microwave radiation is to increase the temperature of the composition and effect the transformation.

The key components of the composition of the invention will have the following functions. The fluent pre-stent composition can be converted to a non-fluent stent composition by the application of a threshold level of microwave energy. Such materials for bioresorbable stents are described in U.S. Ser. No. 08/815,096 which is incorporated herein by reference. Non-bioresorbable or low bioresorbable materials are now envisioned which also can be converted from a fluent to a nonfluent state by application of a threshold level of energy. It is also envisioned to use both bioresorbable and non-bioresorbable materials together.

Such non bioresorbable or low bioresorbable materials include monomers, oligomers and low molecular weight polymers that contain chemically reactive groups that can interact to form covalent bonds together in polymerization, cross-linking or chain extension processes. The mechanisms by which these covalent linkages are formed to include addition reactions mediated by free radical, neutral or cationic intermediates. Examples of free radical mediated addition reactions include thermally or photochemically initiated reaction of acrylate and methacrylate esters, vinyl groups such as styryl and maleic ester groups, and co-reactions of unsaturated esters and vinyl esters. Examples of cationic mediated addition reactions include thermally or photochemically initiated reaction of vinyl ethers. Addition reactions mediated by neutral species include the addition of active hydrogen compounds, such as alcohols or amines, to isocyanate containing species, and the addition of active hydrogen compounds to oxirane groups such as glycidyl ether and glycidyl ester groups (epoxide rings).

The bioresorbability of the final non-fluent products, as well as the overall mechanical integrity of the final stent composition, is largely determined and can be controlled by the selection of the residue comprising the non-reaction portion of the monomer, oligomer or low molecular weight reactive polymer. For example, in reactive oligomers, also called telechelic oligomers or polymers, residues that are readily bioresorbable and biodegradable include those derived from simple hydroxyester, such as glycolide, lactide and caprolactone linkages, anyhydride linkages, spiroester and orthoester linkages. Intermediate biodegradability is achieved through incorporation of carbonate, amide or peptide, or urethane linkages. Low biodegradability is achieved through incorporation of ether and hydrocarbon linkages.

The compositions can also include materials that have a high susceptibility and absorbance for microwave energy. Such materials include, but are not limited to, metal oxides, such as ferric oxide, and carboniferous materials, such as acetylene black and graphite, or hydroxyl containing materials, such as alcohols or water.

Optionally, for systems that solidify by forming covalent bonds mediated by free radical species, a thermally activated free radical initiator and optionally an accelerator may be included in the composition. Such thermal initiation materials include, but are not limited to, a peroxide material like benzoyl peroxide or lauroyl peroxide or ammonium persulfate, or an azo material, such as azo bis(isobutylnitrile) (AIBN, Vazo 64). Accelerator materials include, but are not limited to, reductants such as amines, like triethanol amine (TEOA), alpha hydroxy ketones, like benzoin and acetoin, and ascorbic acid and derivatives.

The fluent pre-stent material may be formed of one or more components which can be transformed from a fluent to a non-fluent state. In one embodiment, the fluent pre-stent material is a single component which undergoes a liquid to solid phase change. In another embodiment, the fluent pre-stent composition is a single component which undergoes a chemical reaction to form a different, non-fluent composition. This chemical reaction may be stimulated by the introduction of a catalyst and/or energy to trigger the transformation. In yet another embodiment, the fluent pre-stent composition is formed of two or more components. These components may react with each other to form a non-fluent composition upon contact, or with the assistance of a chemical catalyst and/or energy.

In an aspect of the invention, the conditions under which the fluent pre-stent composition is converted to a non-fluent stent composition can be used to govern the final physical properties of the stent, such as morphology and modulus. Thus, the mold cavity formed by the balloon surface and surrounding endovascular wall can function much as a batch reactor for conducting a chemical or photochemical reaction. Reaction parameters such as the pressure, temperature and times for injecting reactor fluids into the mold can be controlled in accordance with techniques which are well known to ensure that a desired modulus, homogeneity, or physical property is imparted to the stent being formed in the mold.

The fluent pre-stent composition can be formulated from any one or more components which have the necessary biocompatible properties and which can be converted in situ to a non-fluent stent composition. The fluent pre-stent composition is preferably capable of interlinking with fissures and breaks in living tissue. The fluent pre-stent composition also preferably can penetrate pores of living tissue and can repair an endovascular luminal surface.

A preferred fluent stent composition that may be used in the present invention includes a protein, glycoprotein and/or polysaccharide. The fluent pre-stent composition also preferably includes a liquid vehicle electrolyte capable of dissolving or suspending the protein, glycoprotein or polysaccharide.

The liquid vehicle electrolyte can include an aqueous solution with sufficient ionic strength to conduct electric current or RF energy. Preferably the liquid vehicle electrolyte comprises water and ionized inorganic or organic based salts or poly-salts.

Optionally, the fluent pre-stent composition also includes an insoluble network reinforcement agent. Optionally, the fluent pre-stent composition also includes adjuvants to promote wound healing. Optionally, the fluent pre-stent composition also includes adjuvants which are preferentially resorbed by the body, leaving behind a stent of certain porosity.

Examples of compositions which can be used for the stent composition include a matrix material comprising a protein, glyco-protein or polysaccharide: collagen, fibrin, elastin, fibronectin, vironectin, aglin, albumin, laminin, gelatin, cellulose, modified cellulose, starch, modified starch, synthetic polypeptide; acetylated, sulfonated or phosphorylated collagen, glycosaminoglycans (heparin, heparan, dermatan, chrondoin sulfate). Optionally, the composition can include a liquid vehicle electrolyte comprising aqueous saline or calcium chloride. Optionally, the composition can include a reinforcing material comprising poly(lactide), poly(glycolide), poly (lactide)-co-(glycolide), poly (caprolactone), poly (betahydroxtbutylate), a poly (anhydride), or a poly (orthoester).

A liquid vehicle electrolyte can be advantageously used if RF energy is the source of activation energy applied to effect the change of the pre-stent composition from a fluent to a non-fluent state. If the ionic strength of aqueous saline or calcium chloride is high enough, the electrolyte can also assist in lysing some of the cells. This advantageously may provide a tissue surface that is more readily interpenetrated and bondable by the stent composition as it becomes non-fluent. The matrix materials and liquid vehicle electrolyte are the compositions which most often can be used for the pre-stent composition.

A fluent pre-stent composition that would be expected to respond to RF energy and effect a change of state from a fluent to a non-fluent composition preferably should preferably have the following properties. It should contain ample hydrogen bonding sites. It should preferably contain ionized groups. It should be able to interpenetrate with and form good interactions with tissue structures and tissue components such as proteins, etc. It should exhibit structural regularity (for example, helix forms) for inducing fibril formation and interfibril association. It should provide reactive sites for covalent bonding of the stent composition to surrounding tissue and of the stent composition to itself to form an internal network. Examples are the epsilon amino group on lysine, the hydroxy group on hydroxy proline and other equivalent compositions.

Physically, the fleunt pre-stent composition preferably undergoes a change of state from a fluent state to a non-fluent state upon the application of activation energy of a predetermined threshold for initiating the change of state. The change of state is effected by a microstructural transformation such as the changing of a lattice network in response to a temperature above the activation threshold as is well known. In the case of a photo polymer or photo-forming agent, the activation energy comprises optical energy having a sufficient intensity to effect photo initiation and/or photo polymerization in accordance with techniques which are well known.

If the material is soluble, it should become insoluble or merely swellable in the vehicle electrolyte. If the fluent pre-stent composition is insoluble, but a suspension or emulsion, it should become coagulated and not be resuspendable when in solid form. Rheologically, the preferred material should become more elastic with greater out of phase shear stress response. A net volume contraction should be observable due to loss of the aqueous vehicle to tissue and air as well as conformational changes and chemical shrinkage from cross-linking.

In one embodiment, the fluent pre-stent material includes magnesium sulfate ($MgSO_4$) which serves to dilate the vessel wall to facilitate expansion of the vessel wall. The magnesium sulfate may also be used to enhance the conductivity of the fluent pre-stent material, for example when RF energy is used.

In a preferred embodiment, the material that comprises the body of the stent consists of four components; a protein; a glycoprotein or polysaccharide, a liquid vehicle electrolyte added for conducting RF energy to effect the change of state from a flowable material to a solid, an insoluble yet bioresorbable network reinforcement agent and an adjuvant to promote wound healing such as heparin or its derivatives.

A practical application of the present invention that has value within the technological arts is the treatment of stenosed or otherwise injured endovascular wall of a vas. Further, the present invention is useful in conjunction with the treatment of other lumen, or the like. There are virtually innumerable uses for the present invention, all of which need not be detailed here.

All the disclosed embodiments of the invention described herein can be realized and practiced without undue experimentation. Although the best mode for carrying out the invention contemplated the inventors is discussed above, practice of the present invention is not limited thereto. It will be manifested at various editions, modifications, and rearrangements of the features of the present invention may be made without deviating from the spirit and scope of the underlying inventive concept. Accordingly, it will be appreciated by those skilled in the art that the invention may be practiced otherwise than as specifically described herein. For example, the individual components need be formed in the disclosed shapes, or assembled in the disclosed configuration, but could be provided in virtually any shape, and assembled in virtually any configuration. Further, the individual components need not be fabricated from the disclosed materials, but could be fabricated from virtually any suitable biocompatible materials.

Moreover, although the catheter disclosed is described as a physical separate module, it will be manifest that the catheter may be integrated into other apparatus with which it is associated. Further, all the disclosed elements and features of each disclosed embodiment can be combined with, or substituted for, the disclosed elements and features of every other disclosed embodiment except where such elements or features are mutually exclusive.

It is intended that the appended claims cover all such additions, modifications and rearrangements. The claims are not to be construed as including means-plus-function limitations, unless such limitations are explicitly recited in the claims. Expedient embodiments of the present invention are differentiated by the appended subclaims.

What is claimed is:

1. A method for forming a stent within a body lumen comprising:

advancing a distal catheter body within a body lumen to a section of the body lumen at which a stent is to be formed;

expanding one or more expandable members attached to the distal catheter body such that sections of the body lumen proximal and distal to the stent formation section of the body lumen are occluded, the distal catheter body in combination with the body lumen defining a mold space;

delivering a fluent pre-stent composition within the mold space from outside the body lumen such that the pre-stent composition is continuously in fluent state during pre-stent composition delivery from outside the body lumen to the mold space; and transforming the fluent pre-stent composition to a non-fluent stent composition to form a stent within the mold space.

2. The method according to claim 1, further including the step of radially expanding the stent formation section of the body lumen prior to the transforming step.

3. The method according to claim 1, further including the step of performing balloon angioplasty prior to expanding the one or more expandable members.

4. The method according to claim 3 wherein balloon angioplasty is performed by expanding a member distal to the distal catheter body.

5. The method according to claim 3 wherein balloon angioplasty is performed by expanding a member proximal to the distal catheter body.

6. The method according to claim 3 wherein balloon angioplasty is performed by expanding a member attached to the distal catheter body.

7. The method according to claim 6 wherein the balloon angioplasty expandable member is positioned within one or more of the expandable members used to define the mold space.

8. The method according to claim 1 wherein the one or more expandable members create a mold space which is narrower at the proximal and distal sections of the body lumen than between the proximal and distal sections.

9. The method according to claim 1, wherein the step of transforming includes delivering energy within the mold space to accelerate the transformation.

10. The method according to claim 9, wherein the energy is electromagnetic radiation.

11. The method according to claim 9, wherein the energy is light energy.

12. The method according to claim 9, wherein the energy is RF energy.

13. The method according to claim 9, wherein the energy is microwave energy.

14. The method according to claim 1, further including the step of providing bypass during occlusion of the body lumen.

15. The method according to claim 14, wherein providing bypass including opening a bypass lumen in the distal catheter body by expanding the one or more expandable members.

16. A method for forming a stent within a body lumen comprising:

advancing a distal catheter body within a body lumen to a section of the body lumen at which a stent is to be formed;

expanding one or more expandable members attached to the distal catheter body such that sections of the body lumen proximal and distal to the stent formation section of the body lumen are occluded, the distal catheter body in combination with the body lumen defining a mold space;

delivering a fluent pre-stent composition within the mold space from outside the body lumen such that the pre-stent composition is continuously in fluent state during pre-stent composition delivery from outside the body lumen to the mold space; and delivering microwave energy within the mold space to accelerate the transformation transforming the fluent pre-stent composition to a non-fluent stent composition to form a stent within the mold space.

17. The method according to claim 16, wherein the microwave energy is delivered within the mold space using an antenna attached to the distal catheter body.

18. The method according to claim 16, wherein the microwave energy is delivered within the mold space using an antenna on a guide wire passing through a guide wire lumen in the distal catheter body.

19. The method according to claim 16, wherein the pre-stent composition includes a microwave energy susceptible composition which preferentially absorbs the microwave energy.

20. The method according to claim 19, wherein the microwave energy susceptible composition includes a material selected from the group consisting of tantalum, tantalum oxides, hematite ($\alpha$-$Fe_2O_3$), maghemite ($\gamma$-$Fe_2O_3$), magnetite ($Fe_3O_4$), geothite ($\alpha$-FeOOH), lepidocrocite ($\gamma$-FeOOH), ferrihydrite, feroxyhyte ($\delta$-FeOOH), akageneite ($\beta$-FeOOH), graphite and amorphous carbon.

21. A method for forming a fenestrated stent within a body lumen comprising:

advancing a distal catheter body within a body lumen to a section of the body lumen at which a stent is to be formed;

expanding one or more expandable members attached to the distal catheter body such that sections of the body lumen proximal and distal to the stent formation section of the body lumen are occluded, the distal catheter body in combination with the body lumen defining a mold space, the distal catheter body including one or more members extending from the distal catheter body which define a fenestration pattern within the mold space;

delivering a fluent pre-stent composition within the mold space from outside the body lumen such that the pre-stent composition is continuously in fluent state during pre-stent composition delivery from outside the body lumen to the mold space; and transforming the fluent pre-stent composition to a non-fluent stent composition to form a fenestrated stent within the mold space.

22. The method according to claim 21 wherein the fenestration pattern defining members define a fenestration pattern selected from the group consisting of one or more slits, holes, spirals, helixes, and double helixes.

23. A method for forming a fenestrated stent within a body lumen comprising:

advancing a distal catheter body within a body lumen to a section of the body lumen at which a stent is to be formed;

expanding one or more expandable members attached to the distal catheter body such that sections of the body lumen proximal and distal to the stent formation section of the body lumen are occluded, the distal catheter body in combination with the body lumen defining a mold space, the distal catheter body including one or more detachable members extending from the distal catheter body which define a fenestration pattern within the mold space;

delivering a fluent pre-stent composition within the mold space from outside the body lumen such that the pre-stent composition is continuously in fluent state during pre-stent composition delivery from outside the body lumen to the mold space;

transforming the fluent pre-stent composition to a non-fluent stent composition to form a fenestrated stent within the mold space; and detaching the one or more fenestration pattern defining members from the distal catheter body.

24. The method according to claim 23 wherein the one or more fenestration pattern defining members define a fenestration pattern selected from the group consisting of one or more slits, holes, spirals, helixes, and double helixes.

25. The method according to claim 23 wherein the one or more detachable fenestration pattern defining members are bioresorbable, the method further including the step of bioresorbing the one or more members to leave fenestrations in the stent.

26. The method according to claim 25, wherein bioresorption of the bioresorbable composition leave pores in the stent for the diffusion of biological material therethrough.

27. The method according to claim 25, wherein the step further includes moving the distal catheter body from the section of the body lumen at which the stent was formed, the one or more fenestration pattern defining members being detached in the process of moving the distal catheter body.

28. The method according to claim 27, wherein the one or more detachable fenestration pattern defining members are also separated from the fenestrated stent in the process of moving the distal catheter body.

* * * * *